US011524169B2

(12) United States Patent
Grinberg et al.

(10) Patent No.: US 11,524,169 B2
(45) Date of Patent: Dec. 13, 2022

(54) CHARGE BALANCED CARDIAC PACING FROM HIGH VOLTAGE CIRCUITRY OF AN EXTRA-CARDIOVASCULAR IMPLANTABLE CARDIOVERTER DEFIBRILLATOR SYSTEM

(71) Applicant: Medtronic, Inc., Minneapolis, MN (US)

(72) Inventors: Yanina Grinberg, Plymouth, MN (US); Paul D. Baker, Oakdale, MN (US); Lonny V. Cabelka, San Clemente, CA (US); Craig W. Dorma, Albertville, MN (US); Timothy A. Ebeling, Circle Pines, MN (US); Michael W. Heinks, New Brighton, MN (US); James Vander Heyden, Maplewood, MN (US); Joseph Ippolito, Minneapolis, MN (US); Joel R. Lauer, Clearwater, MN (US); Robert W. Sawchuk, Roseville, MN (US); Brian W. Schousek, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 1492 days.

(21) Appl. No.: 15/425,169

(22) Filed: Feb. 6, 2017

(65) Prior Publication Data

US 2018/0221677 A1 Aug. 9, 2018

(51) Int. Cl.
*A61N 1/39* (2006.01)
*A61N 1/05* (2006.01)
*A61N 1/365* (2006.01)

(52) U.S. Cl.
CPC ............. *A61N 1/3962* (2013.01); *A61N 1/05* (2013.01); *A61N 1/36507* (2013.01);
(Continued)

(58) Field of Classification Search
CPC ........ A61N 1/378; A61N 1/39; A61N 1/3962; A61N 1/3621; A61N 1/3782; A61N 1/3981; A61N 1/3627; A61N 1/3975
(Continued)

(56) References Cited

U.S. PATENT DOCUMENTS 4,543,956 A 10/1985 Herscovici
5,184,616 A 2/1993 Weiss
(Continued)

OTHER PUBLICATIONS (PCT/US2018/016337) PCT Notification of Transmittal of the International Search Report and the Written Opinion of the International Searching Authority, dated May 16, 2018, 10 pages.
(Continued)

*Primary Examiner* — Jon Eric C Morales

(57) ABSTRACT

An extra-cardiovascular implantable cardioverter defibrillator (ICD) having a high voltage therapy module is configured to control a high voltage charging circuit to charge a capacitor to a pacing voltage amplitude to deliver charge balanced pacing pulses. The capacitor is chargeable to a shock voltage amplitude that is greater than the pacing voltage amplitude. The ICD is configured to enable switching circuitry of the high voltage therapy module to discharge the capacitor to deliver a first pulse having a first polarity and a leading voltage amplitude corresponding to the pacing voltage amplitude for pacing the patient's heart via a pacing electrode vector selected from extra-cardiovascular electrodes. The high voltage therapy module delivers a second pulse after the first pulse. The second pulse has a second polarity opposite the first polarity and balances the electrical charge delivered during the first pulse.

42 Claims, 14 Drawing Sheets

(52) U.S. Cl.
CPC ......... *A61N 1/3925* (2013.01); *A61N 1/3981* (2013.01); *A61N 1/3987* (2013.01); *A61N 1/39622* (2017.08)

(58) Field of Classification Search
USPC ........................................................ 607/4, 7
See application file for complete search history.

(56) References Cited

U.S. PATENT DOCUMENTS

| | | | |
|---|---|---|---|
| 5,352,239 A | 10/1994 | Pless | |
| 5,354,316 A | 10/1994 | Keimel | |
| 5,383,908 A * | 1/1995 | Sweeney | A61N 1/3918 607/5 |
| 5,531,765 A | 7/1996 | Pless | |
| 5,545,186 A | 8/1996 | Olson et al. | |
| 5,591,209 A | 1/1997 | Kroll | |
| 5,601,612 A | 2/1997 | Gliner et al. | |
| 5,620,470 A | 4/1997 | Gliner et al. | |
| 5,735,879 A | 4/1998 | Gliner et al. | |
| 5,749,905 A | 5/1998 | Gliner et al. | |
| 5,776,166 A | 7/1998 | Gliner et al. | |
| 5,836,978 A | 11/1998 | Gliner et al. | |
| 6,047,212 A | 4/2000 | Gliner et al. | |
| 6,298,266 B1 | 10/2001 | Rubin et al. | |
| 6,393,316 B1 | 5/2002 | Gillberg et al. | |
| 6,757,561 B2 | 6/2004 | Rubin et al. | |
| 7,031,771 B2 | 4/2006 | Brown et al. | |
| 7,174,208 B2 | 2/2007 | DeGroot et al. | |
| 7,349,735 B2 | 3/2008 | Rubin et al. | |
| 7,761,150 B2 | 7/2010 | Ghanem et al. | |
| 7,899,530 B2 | 3/2011 | Rubin et al. | |
| 8,027,721 B2 | 9/2011 | Sullivan | |
| 8,121,680 B2 | 2/2012 | Falkenberg et al. | |
| 8,145,303 B2 | 3/2012 | Rubin et al. | |
| 8,160,684 B2 | 4/2012 | Ghanem et al. | |
| 8,195,291 B2 | 6/2012 | Norton et al. | |
| 8,437,842 B2 | 5/2013 | Zhang et al. | |
| 9,186,516 B2 | 11/2015 | Mower | |
| 2002/0035376 A1 | 3/2002 | Bardy et al. | |
| 2002/0049476 A1 | 4/2002 | Bardy et al. | |
| 2002/0091414 A1 | 7/2002 | Bardy et al. | |
| 2002/0095184 A1 | 7/2002 | Bardy et al. | |
| 2002/0107544 A1 | 8/2002 | Ostroff et al. | |
| 2002/0120299 A1 | 8/2002 | Ostroff et al. | |
| 2004/0158292 A1 | 8/2004 | Sheldon et al. | |
| 2010/0204766 A1 * | 8/2010 | Zdeblick | A61N 1/056 607/119 |
| 2012/0123492 A1 | 5/2012 | Hunt et al. | |
| 2013/0035735 A1 | 2/2013 | Kroll | |
| 2014/0121716 A1 | 5/2014 | Casavant et al. | |
| 2014/0277259 A1 * | 9/2014 | Rosenberg | A61N 1/36071 607/46 |
| 2015/0306375 A1 | 10/2015 | Marshall et al. | |
| 2015/0306410 A1 | 10/2015 | Marshall et al. | |
| 2016/0030742 A1 | 2/2016 | Mower | |
| 2016/0106991 A1 | 4/2016 | Stadler et al. | |
| 2016/0158567 A1 * | 6/2016 | Marshall | A61N 1/3962 600/373 |
| 2016/0339248 A1 | 11/2016 | Schrock et al. | |
| 2017/0173346 A1 * | 6/2017 | Kane | A61N 1/37217 |

OTHER PUBLICATIONS

Anderson et al., "Extra-Cardiovascular Pacing Using High-Voltage Therapy Circutry of an Mplantable Cardioverter Defibrillator", U.S. Appl. No. 62/462,499, filed Dec. 3, 2015, 72 pages.
Anderson et al., "Extra-Cardiovascular Pacing by an Implantable Cardioverter Defibrillator", U.S. Appl. No. 15/367,516, filed Dec. 2, 2016, 82 pages.
Anderson et al., "Extra-Cardiovascular Pacing Using High-Voltage Therapy Circuitry of an Implantable Cardioverter Defibrillator", U.S. Appl. No. 15/367,777, filed Dec. 2, 2016, 54 pages.
Anderson et al., "Extra-Cardiovascular Cardiac Pacing System for Delivering Composite Pacing Pulses", U.S. Appl. No. 62/262,412, filed Dec. 3, 2015, 70 pages.
Anderson et al., "Extra-Cardiovascular Cardiac Pacing System for Delivering Composite Pacing Pulses", U.S. Appl. No. 15/368,197, filed Dec. 2, 2016, 77 pages.
Nikolski et al., "Tachyarrhythmia Induction by an Extra-Cardiovascular Implantable Cardioverter Defibrillator", U.S. Appl. No. 62/262,500, filed Dec. 3, 2015, 58 pages.
Nikolski et al., "Tachyarrhythmia Induction by an Extra-Cardiovascular Implantable Cardioverter Defibrillator", U.S. Appl. No. 15/367,448, filed Dec. 2, 2016, 73 pages.
Grinberg et al., "Asystole Detection and Response in an Implantable Cardioverter Defibrillator ", U.S. Appl. No. 62/328,803, filed Apr. 28, 2016, 76 pages.
Grinberg et al., "Asystole Detection and Response in an Implantable Cardioverter Defibrillator ", U.S. Appl. No. 15/142,074, filed Apr. 29, 2016, 76 pages.

* cited by examiner

CHARGE BALANCED CARDIAC PACING FROM HIGH VOLTAGE CIRCUITRY OF AN EXTRA-CARDIOVASCULAR IMPLANTABLE CARDIOVERTER DEFIBRILLATOR SYSTEM

TECHNICAL FIELD

The disclosure relates generally to an extra-cardiovascular implantable cardioverter defibrillator (ICD) system, device and method for delivering charge balanced cardiac pacing pulses from a high voltage therapy module using extra-cardiovascular electrodes.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation.

SUMMARY

In general, the disclosure is directed to techniques for delivering charge balanced cardiac pacing pulses to a patient's heart by a cardiac defibrillation system, such as an extra-cardiovascular ICD system. An ICD operating according to the techniques disclosed herein delivers charge balanced cardiac pacing pulses using extra-cardiovascular electrodes carried by a medical electrical lead extending from the ICD. The ICD includes a high voltage therapy module capable of delivering high voltage shock pulses for terminating tachycardia or fibrillation. The high voltage therapy module is controlled to deliver charge balanced pacing pulses when a need for pacing is detected. In some examples, charge balanced pacing pulses are delivered instead of non-charge balanced pacing pulses when charge balanced pacing criteria are satisfied.

In one example, the disclosure provides an extra-cardiovascular ICD system including a sensing module configured to receive a cardiac electrical signal from a patient's heart, a high voltage therapy module and a control module. The high voltage therapy module includes a capacitor chargeable to a shock voltage amplitude for delivering cardioversion/defibrillation shocks in response to detecting a shockable rhythm, e.g., ventricular tachycardia or ventricular fibrillation. The high voltage therapy module further includes a high voltage charging circuit configured to charge the capacitor to the shock voltage amplitude and switching circuitry configured to couple first capacitor to a pacing electrode vector selected from implantable extra-cardiovascular electrodes. The control module is coupled to the sensing module and the high voltage therapy module and configured to detect a need for cardiac pacing from the cardiac electrical signal. In response to detecting the need for cardiac pacing, the control module controls the high voltage therapy module to deliver at least one charge balanced cardiac pacing pulse via the pacing electrode vector by controlling the high voltage charging circuit to charge the first capacitor to a pacing voltage amplitude that is less than the shock voltage amplitude, enabling the switching circuitry to discharge the first capacitor to deliver a first pulse having a first polarity and a leading voltage amplitude corresponding to the pacing voltage amplitude for pacing the patient's heart, and controlling the high voltage therapy module to deliver a second pulse after the first pulse. The second pulse is delivered having a second polarity opposite the first polarity and balances the electrical charge delivered during the first pulse.

In another example, the disclosure provides a method performed by an extra-cardiovascular ICD. The method includes receiving a cardiac electrical signal by a sensing module of the ICD from a patient's heart and detecting a need for cardiac pacing by a control module of the ICD from the cardiac electrical signal. In response to detecting the need for cardiac pacing, the method includes controlling a high voltage therapy module of the ICD to deliver at least one charge balanced cardiac pacing pulse by controlling a high voltage charging circuit to charge a capacitor to a pacing voltage amplitude. The capacitor is also chargeable to a shock voltage amplitude that is greater than the pacing voltage amplitude for delivering cardioversion/defibrillation shocks in response to detecting a shockable rhythm, e.g., ventricular tachycardia or ventricular fibrillation. The method further includes switching circuitry of the high voltage therapy module to discharge the first capacitor to deliver a first pulse having a first polarity and a leading voltage amplitude corresponding to the pacing voltage amplitude for pacing the patient's heart via a pacing electrode vector selected from implantable extra-cardiovascular electrodes, and controlling the high voltage therapy module to deliver a second pulse after the first pulse. The second pulse is delivered having a second polarity opposite the first polarity and balances the electrical charge delivered during the first pulse.

In another example, the disclosure provides a non-transitory, computer-readable storage medium storing a set of instructions which, when executed by a control module of an extra-cardiovascular ICD cause the ICD to receive a cardiac electrical signal by a sensing module of the ICD from a patient's heart; detect a need for cardiac pacing of the ICD from the cardiac electrical signal; in response to detecting the need for cardiac pacing, control a high voltage therapy module of the ICD to deliver at least one charge balanced cardiac pacing pulse. The high voltage therapy module is controlled to deliver the charge balanced cardiac pacing pulse by controlling a high voltage charging circuit to charge a capacitor to a pacing voltage amplitude; enabling switching circuitry of the high voltage therapy module to discharge the first capacitor to deliver a first pulse having a first polarity and a leading voltage amplitude corresponding to the pacing voltage amplitude for pacing the patient's heart via a pacing electrode vector selected from implantable extra-cardiovascular electrodes; and controlling the high voltage therapy module to deliver a second pulse after the first pulse, the second pulse having a second polarity opposite the first polarity, the second pulse balancing the electrical charge delivered during the first pulse. The capacitor is also chargeable to a shock voltage amplitude that is greater than the pacing voltage amplitude for delivering cardioversion/defibrillation shocks in response to detecting a shockable rhythm, e.g., ventricular tachycardia or ventricular fibrillation.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for delivering charge balanced cardiac pacing pulses using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue.

Pacing pulses that are not charge balanced can lead to electrode corrosion over time and cause polarization artifact that can interfere with sensing of cardiac electrical signals. Charge balanced pacing pulses may minimize these effects. In extra-cardiovascular ICD systems, the high voltage (HV) therapy module used for delivering high voltage cardioversion/defibrillation (CV/DF) shocks may be required for delivering cardiac pacing pulses since the pacing capture threshold of an extra-cardiovascular pacing electrode vector may be significantly higher than the pacing capture threshold of a transvenous, endocardial or epicardial pacing electrode vector. The HV therapy module of ICDs is generally configured to deliver monophasic, biphasic or other pulse waveforms for delivering a high voltage CV/DF shock, but since these pulses are delivered relatively infrequently, non-charge balanced CV/DF pulses may be delivered without the concerns of electrode corrosion over time or sensing artifacts that may be associated with non-charge balanced cardiac pacing. The techniques disclosed herein provide a method performed by an ICD for delivering charge balanced cardiac pacing pulses via implanted extra-cardiovascular electrodes by a HV therapy module that is also used for delivering CV/DF shocks.

Figure 1A:
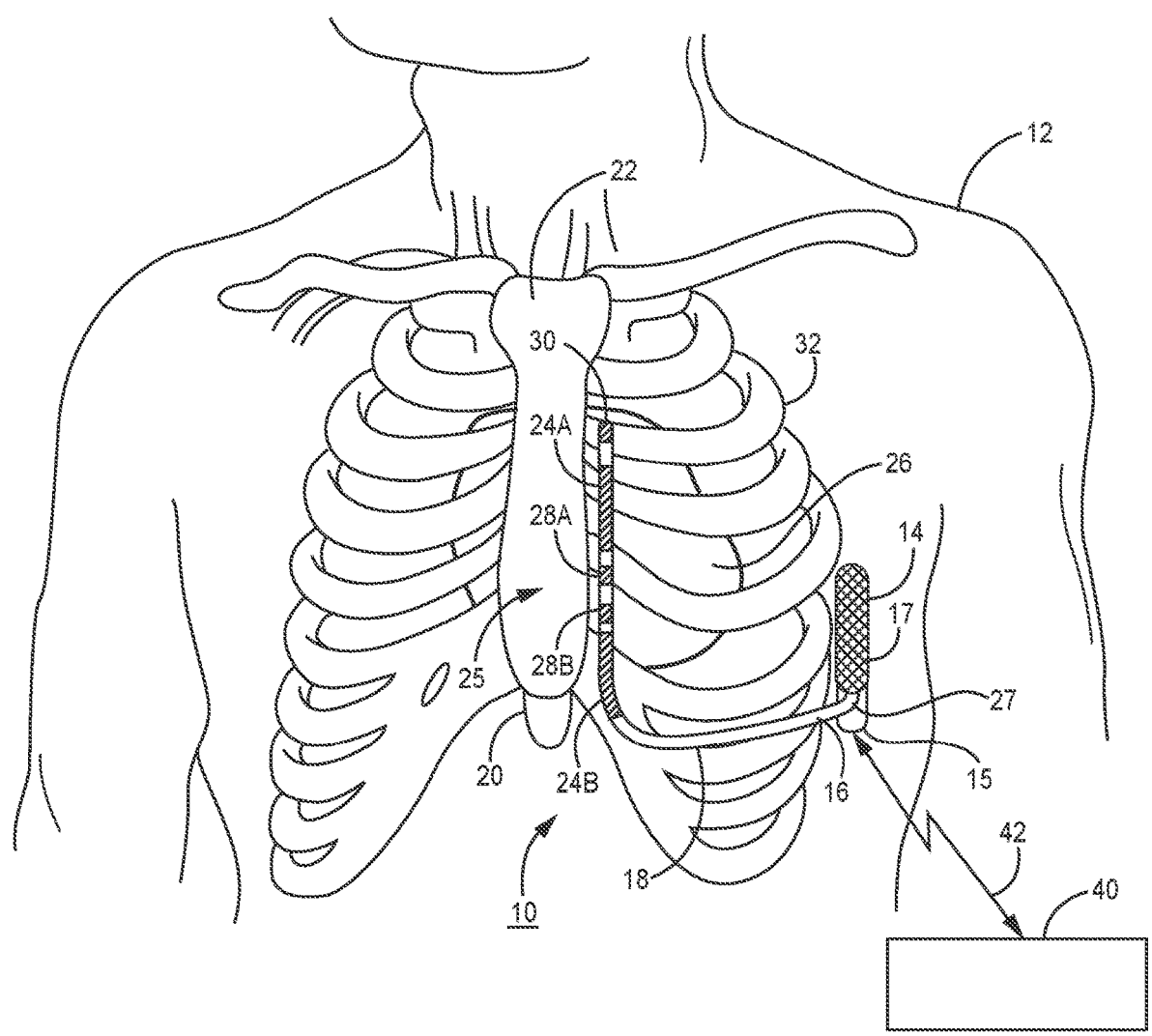
FIGS. 1A and 1B are conceptual diagrams of an extra-cardiovascular ICD system according to one example.
Figure 1B:
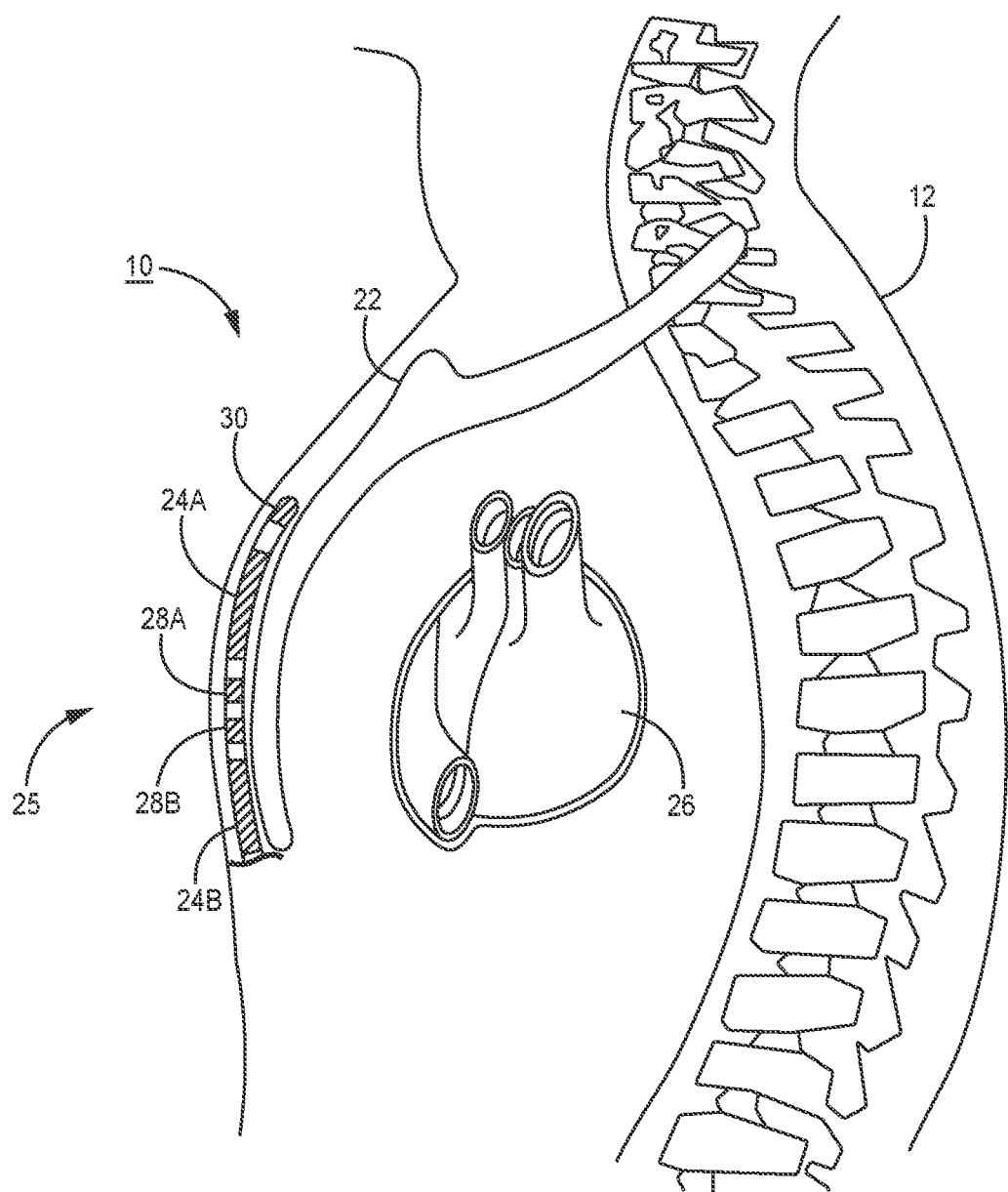

FIGS. 1A and 1B are conceptual diagrams of an extra-cardiovascular ICD system 10 according to one example. FIG. 1A is a front view of ICD system 10 implanted within patient 12. FIG. 1B is a side view of a portion of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a "can" electrode). In examples described herein, housing 15 may be used as an active can electrode for use in delivering high voltage CV/DF shocks and relatively lower voltage cardiac pacing pulses generated by a high voltage therapy module. The housing 15 of ICD 14 may include a plurality of electrodes on an outer portion of the housing instead of acting as a single electrode. The outer portion(s) of the housing 15 functioning as an electrode(s) may be coated with a material, such as titanium nitride for reducing polarization artifact.

ICD 14 includes a connector assembly 17 (also referred to as a connector block or header) that includes electrical feedthroughs crossing housing 15 to provide electrical connections between conductors extending within an elongated lead body 18 of lead 16 and electronic components included within the housing 15 of ICD 14. As will be described in further detail herein, housing 15 may house one or more processors, memories, transceivers, sensors, electrical signal sensing circuitry, therapy delivery circuitry, power sources and other appropriate components.

Elongated lead body 18 includes a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24A and 24B, collectively 24, and pace/sense electrodes 28A, 28B, and 30. In some cases, defibrillation electrodes 24A and 24B may together form a defibrillation electrode in that they are configured to be activated concurrently for delivering electrical stimulation pulses including CV/DF shocks and cardiac pacing pulses such as the charge balanced pacing pulses described herein. Alternatively, defibrillation electrodes 24A and 24B may form separate defibrillation electrodes in which case each of the electrodes 24A and 24B may be activated independently for delivering electrical stimulation pulses. In some instances, defibrillation electrodes 24A and 24B are coupled to electrically isolated conductors, and ICD 14 may include switching mechanisms to allow electrodes 24A and 24B to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24A and 24B (and in some example housing 15) are referred to as defibrillation electrodes because they are utilized, individually or collectively, for delivering high voltage stimulation therapy (e.g., cardioversion or defibrillation shocks). Electrodes 24A and 24B may be elongated coil electrodes and generally have a relatively high surface area for delivering high voltage electrical stimulation pulses compared to low voltage pacing and sensing electrodes. However, electrodes 24A and 24B and housing 15 may also be utilized to provide pacing functionality, sensing functionality or both pacing and sensing functionality in addition to or instead of high voltage cardioversion/defibrillation shock therapy. In this sense, the use of the term "defibrillation electrode" herein should not be considered as limiting the electrodes 24A and 24B to use in only high voltage CV/DF therapy applications. Electrodes 24A and/or 24B may be used in a pacing electrode vector for delivering extra-cardiovascular pacing pulses from a high-voltage therapy module that is also used for delivering CV/DF shocks. As described herein, electrodes 24A and 24B may be used together in a pacing electrode vector, one as the cathode and the other as the anode, or individually as the cathode (or anode) with housing 15 as the anode (or cathode) for delivering charge balanced pacing pulses.

Electrodes 28A, 28B and 30 are relatively smaller surface area electrodes for delivering relatively low voltage pacing pulses and for sensing cardiac electrical signals. Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both.

In the example illustrated in FIGS. 1A and 1B, electrodes 28A and 28B are located between defibrillation electrodes 24A and 24B and electrode 30 is located distal to defibrillation electrode 24A. Electrodes 28A and 28B are illustrated as ring electrodes, and electrode 30 is illustrated as a hemispherical tip electrode in the example of FIGS. 1A and 1B. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion 25 of lead 16. Further, electrodes 28A, 28B, and 30 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14 or other factors.

Electrical conductors (not illustrated) extend through one or more lumens of the elongated lead body 18 of lead 16 from the lead connector at the proximal lead end 27 to respective electrodes 24A, 24B, 28A, 28B, and 30 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 electrically couple the electrodes 24A, 24B, 28A, 28B and 30 to circuitry, such as a therapy module and/or a sensing module, of ICD 14 via connections in the connector assembly 17, including associated electrical feedthroughs crossing housing 15. The electrical conductors transmit therapy from a therapy module within ICD 14 to one or more of defibrillation electrodes 24A and 24B and/or pace/sense electrodes 28A, 28B, and 30 and transmit sensed electrical signals from one or more of defibrillation electrodes 24A and 24B and/or pace/sense electrodes 28A, 28B, and 30 to the sensing module within ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28A, 28B, and 30 may be located elsewhere along the length of lead body 18, e.g., distal to defibrillation electrode 24A, proximal to defibrillation electrode 24B, and/or between electrodes 24A and 24B. For example, lead 16 may include a single pace/sense electrode 28 between defibrillation electrodes 24A and 24B and no pace/sense electrode distal to defibrillation electrode 24A or proximal to defibrillation electrode 24B.

In other examples, lead 16 may include only a single pace/sense electrode 28 between defibrillation electrodes 24A and 24B and include another discrete electrode(s) distal to defibrillation electrode 24A and/or proximal to defibrillation electrode 24B. Various example configurations of extra-cardiovascular leads and electrodes and dimensions that may be implemented in conjunction with the extra-cardiovascular pacing techniques disclosed herein are described in commonly-assigned U.S. Pat. Publication No. 2015/0306375 (Marshall, et al.) and U.S. Pat. Publication No. 2015/0306410 (Marshall, et al.), both of which are incorporated herein by reference in their entirety.

In still other examples, ICD system 10 of FIGS. 1A and 1B may include a second extra-cardiovascular electrical stimulation and sensing lead similar to lead 16. The second lead may, for example, extend laterally to the posterior of patient 12 and include one or more electrodes that form an electrode vector with one or more of electrodes 24A, 24B, 28A, 28B, and/or 30 of lead 16 for providing cardiac pacing in accordance with the techniques disclosed herein.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

In some instances, electrodes 24A, 24B, 28A, 28B, and/or 30 of lead 16 may be shaped, oriented, designed or otherwise configured to reduce extra-cardiac stimulation. For example, electrodes 24A, 24B, 28A, 28B, and/or 30 of lead 16 may be shaped, oriented, designed, partially insulated or otherwise configured to focus, direct or point electrodes 24A, 24B, 28A, 28B, and/or 30 toward heart 26. In this manner, electrical stimulation pulses delivered via lead 16 are directed toward heart 26 and not outward toward skeletal muscle. For example, electrodes 24A, 24B, 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When ICD 14 delivers pacing pulses via electrodes 24A, 24B, 28A, 28B, and/or 30, recruitment of surrounding skeletal muscle by the pacing pulses, which may cause discomfort to the patient, may be reduced by shaping, orienting, or partially insulating electrodes 24 to focus or direct electrical energy toward heart 26.

ICD 14 may obtain electrical signals corresponding to electrical activity of heart 26 via one or more sensing electrode vectors that include a combination of electrodes 28A, 28B, and 30 and the housing 15 of ICD 14. For example, ICD 14 may obtain cardiac electrical signals sensed using a sensing vector between combinations of electrodes 28A, 28B, and 30 with one another or obtain cardiac electrical signals using a sensing vector between any one or more of electrodes 28A, 28B, and 30 and the conductive housing 15 of ICD 14. In some instances, ICD 14 may even obtain cardiac electrical signals using a sensing vector that includes one or both defibrillation electrodes 24A or 24B such as between each other or in combination with one or more of electrodes 28A, 28B, and 30, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF), for detecting a need for cardiac pacing or a CV/DF shock. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety. Other examples of techniques that may be used in analyzing cardiac electrical signals and detecting a need for cardiac pacing or a need for delivering a CV/DF shock are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

ICD 14 generates and delivers electrical stimulation therapy in response to detecting a tachyarrhythmia (e.g., VT or VF). ICD 14 may deliver one or more CV/DF shocks via one or both of defibrillation electrodes 24A and 24B and/or housing 15 if VT or VF is detected. In some therapy protocols anti-tachycardia pacing (ATP) pulses are delivered prior to a CV/DF shock in response to detecting VT and may terminate the VT, precluding the need for a shock.

ICD 14 may generate and deliver cardiac pacing pulses in response to detecting a variety of arrhythmias, including bradycardia pacing pulses, rate responsive pacing, ATP pulses, pacing pulses during ventricular asystole due to atrioventricular conduction block or after a CV/DF shock. In some cases a need for cardiac pacing pulses may be required for inducing a tachyarrhythmia during ICD testing. A pulse burst may be delivered for VF induction or entrainment pacing pulses may be delivered before a T-shock for VF induction. Cardiac pacing pulses may be delivered using an electrode vector that includes one or more of the electrodes 24A, 24B, 28A, 28B and/or 30, and/or the housing 15 of ICD 14. In one example, the high surface area defibrillation electrodes 24A and 24B are used together in a pacing electrode vector. The pacing electrode vector defined by electrodes 24A and 24B has a relatively low impedance which allows relatively greater current to be delivered to the heart for a given pacing pulse width and pacing pulse voltage amplitude compared to the current delivered via a pacing electrode vector that includes a relatively smaller surface area electrode, e.g., electrode 28A, 28B or 30, and consequently a relatively higher impedance. As described below, ICD 14 may be configured to deliver cardiac pacing pulses from a high voltage (HV) therapy module and may control the high voltage therapy module to deliver charge balanced pacing pulses to reduce the long term effects of non-charge balanced pacing pulse delivery on the extra-cardiovascular electrodes and reduce pacing artifact that may interfere with cardiac signal sensing.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth, tissue conduction communication (TCC) or other telemetry protocols.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver cardiac electrical stimulation pulses according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. For example, pacing capture threshold tests may be initiated by a user interacting with external device 40. A user may observe cardiac electrical signals retrieved from ICD 14 on a display of external device 40 for confirming cardiac capture by pacing pulses delivered by ICD 14 during a capture threshold test. External device 40 may alternatively be embodied as a home monitor or hand held device.

Figure 2A:
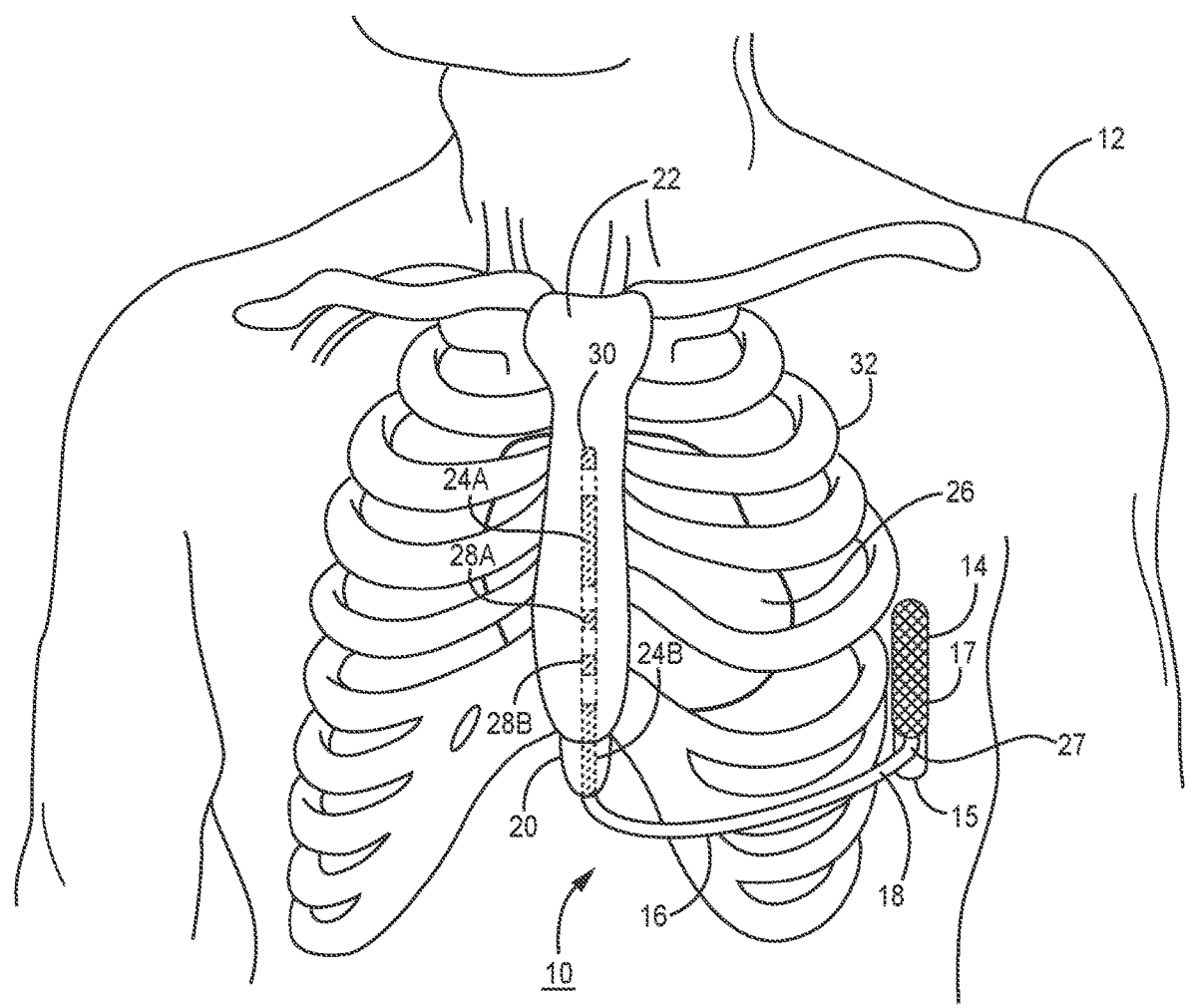
FIGS. 2A-2C are conceptual diagrams of a patient implanted with the extra-cardiovascular ICD system of FIG. 1A in a different implant configuration.
Figure 2B:
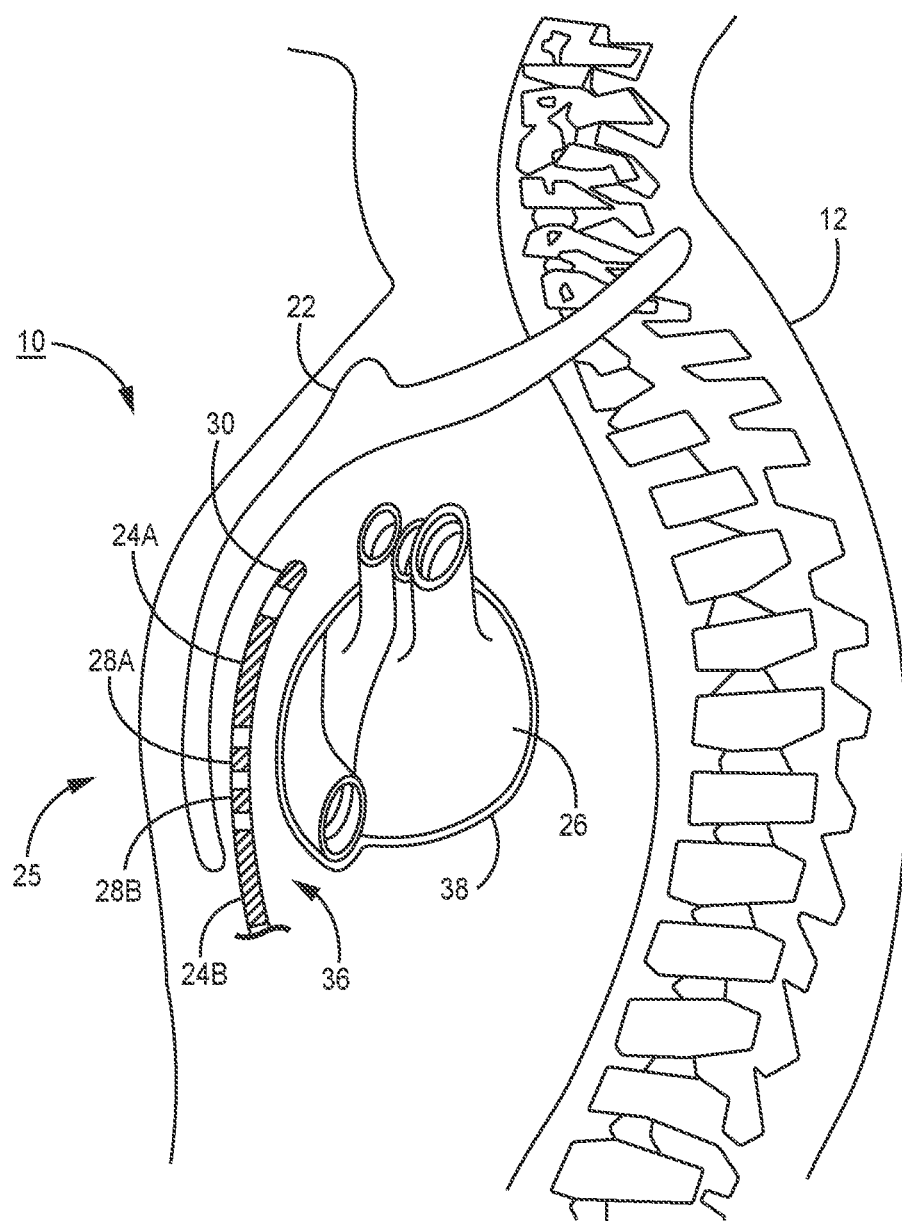
Figure 2C:
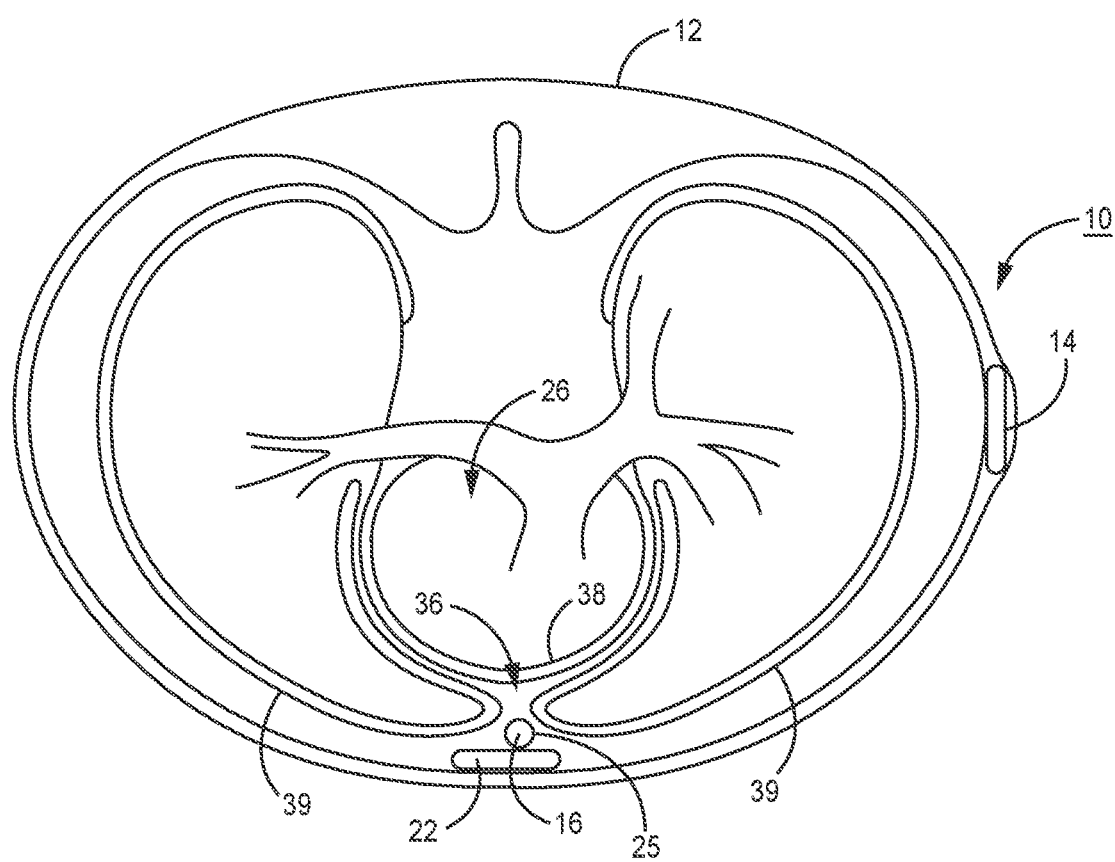

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 26. Other implant locations and lead and electrode arrangements that may be used in conjunction with the cardiac pacing techniques described herein are generally disclosed in the above-incorporated references. Although example extra-cardiovascular locations are described above with respect to FIGS. 1A, 1B and 2A-2C, the cardiac pacing techniques of this disclosure may be utilized in other implementations of extra-cardiovascular pacing applications.

Figure 3:
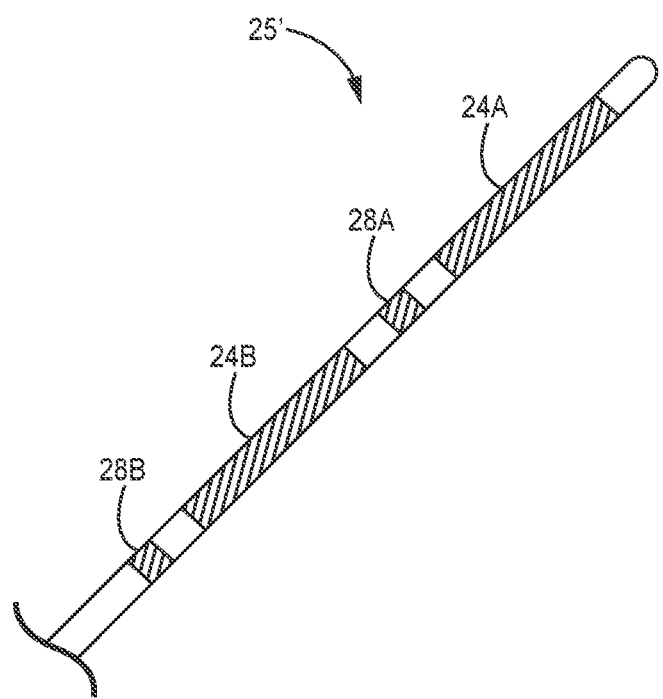
FIG. 3 is a conceptual diagram of a distal portion of an extra-cardiovascular lead having an electrode configuration according to another example.

FIG. 3 is a conceptual diagram illustrating a distal portion 25' of another example of implantable electrical lead 16 having an alternative electrode arrangement. In this example, distal portion 25' includes two pace/sense electrodes 28A and 28B and two defibrillation electrodes 24A and 24B and respective conductors (not shown) to provide the electrical stimulation and sensing functionality as described above in conjunction with FIGS. 1A, 1B and FIGS. 2A-2C. In this example, however, electrode 28B is proximal to proximal defibrillation electrode 24B, and electrode 28A is distal to proximal defibrillation electrode 24B such that electrodes 28A and 28B are separated by defibrillation electrode 24B. In a further example, in addition to electrodes 28A and 28B, lead 16 may include a third pace/sense electrode located distal to defibrillation electrode 24A.

The spacing and location of pace/sense electrodes 28A and 28B may be selected to provide pacing vectors that enable efficient pacing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 3) may be less than or equal to 15 cm and may be less than or equal to 13 cm and or even less than or equal to 10 cm. The spacing and location of pace/sense electrodes 28A and 28B may be selected to provide pacing vectors that enable efficient pacing of heart 26. It is contemplated that one or more pace/sense electrodes may be distal to distal defibrillation electrode 24A, one or more pace/sense electrodes may be between defibrillation electrodes 24A and 24B, and/or one or more pace/sense electrodes may be proximal to proximal defibrillation electrode 24B. Having multiple pace/sense electrodes at different locations along lead body 18 enables selection from among a variety of inter-electrode spacings, which allows a pacing electrode pair (or combination) to be selected having an inter-electrode spacing that results in the greatest pacing efficiency.

ICD 14 may deliver electrical stimulation and/or sense electrical signals using any electrode vector that includes defibrillation electrodes 24A and 24B (individually or collectively), and/or electrodes 28A and/or 28B, and/or the housing 15 of ICD 14. For example, ICD 14 may deliver pacing pulses using a low voltage therapy module via a pacing electrode vector in which one of electrodes 28A or 28B is selected as a cathode and the other of electrodes 28A and 28B is selected as the anode. Other examples of low-voltage therapy delivery electrode vectors may include one of electrodes 28A or 28B or both in combination selected as a cathode (or anode) with one of defibrillation electrodes 24A, 24B or housing 15 selected as an anode (or cathode). When the pacing pulse energy of cardiac pacing pulses generated and delivered by a low voltage therapy module are inadequate to capture the heart, or in an ICD that includes only a high voltage therapy module, ICD 14 may deliver pacing pulses using a high voltage therapy module using a pacing electrode vector that uses defibrillation electrodes 24A and 24B as a cathode and anode pair or uses one or both of defibrillation electrodes 24A and 24B as a cathode (or anode) and the housing 15 of ICD 14 as an anode (or cathode). In some cases, a pacing/sensing electrode 28A, 28B, and/or 30 may be included in a pacing electrode vector used to deliver pacing pulses generated by the high voltage therapy module as described herein. ICD 14 may be configured to determine which pacing vector and which one of a low voltage therapy module and a high voltage therapy module are used to deliver cardiac pacing pulses, e.g., in accordance with the techniques described in provisional U.S. Pat. Application No. 62/262,499 and corresponding pending U.S. patent application Ser. No. 15/367,516, now issued as U.S. Pat. No. 10,080,905 (Anderson, et al.) and U.S. patent application Ser. No. 15/367,777, now issued as U.S. Pat. No. 10,155,119 (Anderson, et al.), all incorporated herein by reference in their entirety.

Figure 4:
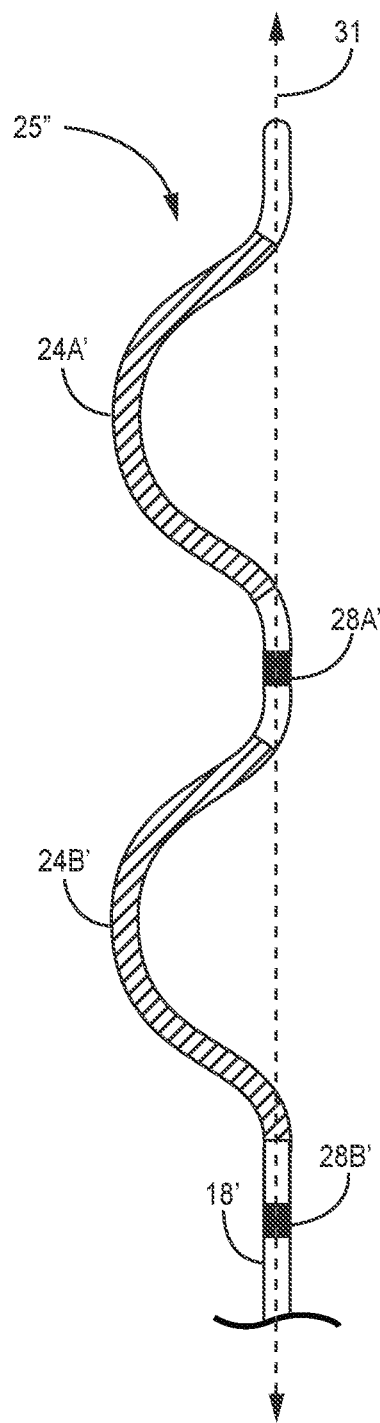
FIG. 4 is a conceptual diagram of a distal portion of an extra-cardiovascular lead having a lead body shape according to another example.

FIG. 4 is a conceptual diagram illustrating a distal portion 25" of another example of extra-cardiovascular lead 16 having an electrode arrangement similar to that of FIG. 3 but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along pre-formed curving portions of the lead body 18'. Pace/sense electrode 28A' is carried between defibrillation electrodes 24A' and 24B'. Pace/sense electrode 28B' is carried proximal to the proximal defibrillation electrode 24B'.

In one example, lead body 18' may be formed having a normally curving distal portion 25" that includes two "C" shaped curves, which together may resemble the Greek letter epsilon, "ε." Defibrillation electrodes 24A' and 24B' are each carried by the two respective C-shaped portions of the lead body distal portion 25" and extend or curve in the same direction. In the example shown, pace/sense electrode 28A' is proximal to the C-shaped portion carrying electrode 24A', and pace/sense electrode 28B' is proximal to the C-shaped portion carrying electrode 24B'. Pace/sense electrodes 24A' and 24B' are approximately aligned with a central axis 31 of the normally straight or linear, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by curving serpentine, undulating or zig-zagging distal portion of the lead body that may be implemented with the pacing techniques described herein are generally disclosed in pending U.S. Pat. Publication No. 2016/0158567, now issued as U.S. Pat. No. 10,675,478 (Marshall, et al.), incorporated herein by reference in its entirety.

Figure 5:
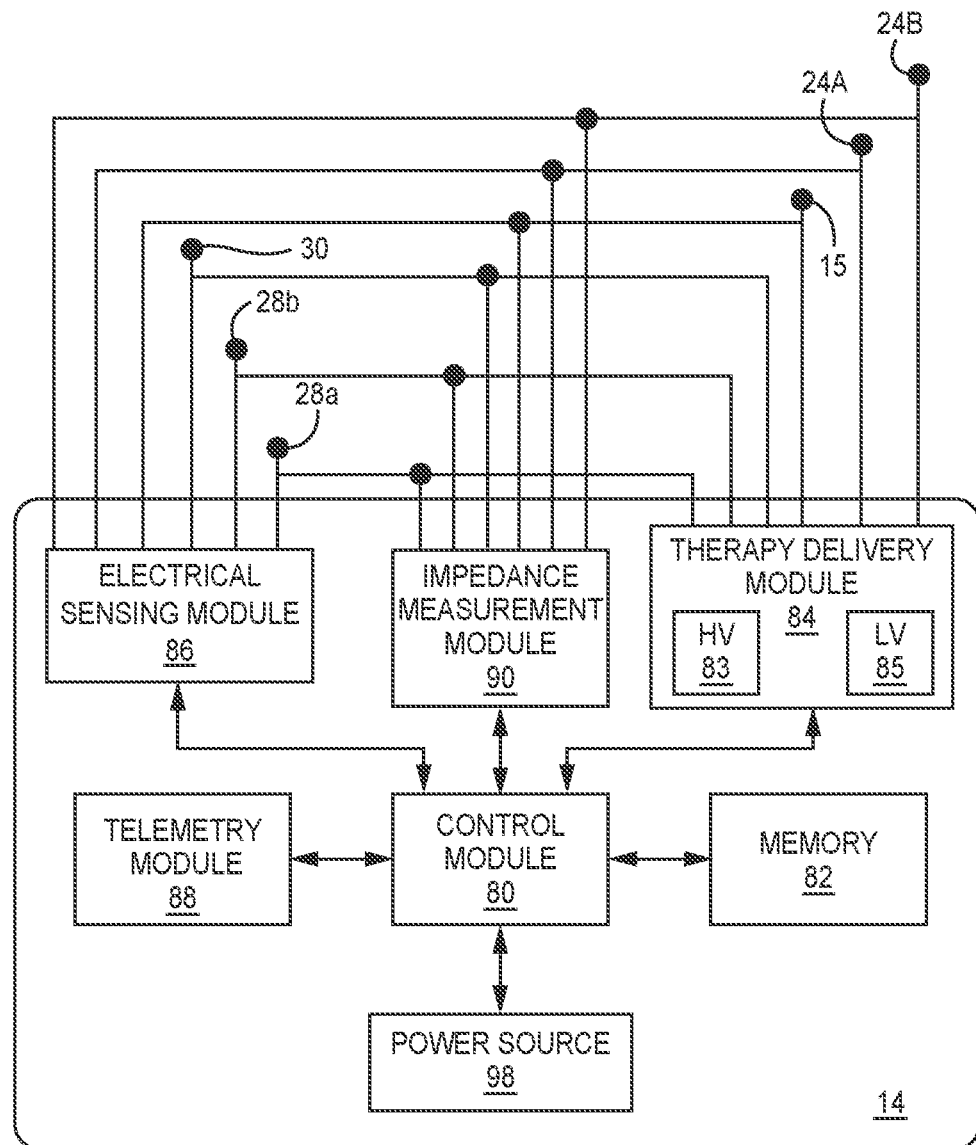
FIG. 5 is a schematic diagram of the ICD of the system of FIGS. 1A-2C according to one example.

FIG. 5 is a schematic diagram of ICD 14 according to one example. The electronic circuitry enclosed within housing 15 (shown schematically as a can electrode in FIG. 5) includes software, firmware and hardware that cooperatively monitor one or more cardiac electrical signals, determine when a pacing therapy is necessary, and deliver prescribed pacing therapies as needed. The software, firmware and hardware are also configured to determine when a CV/DF shock is necessary, and deliver prescribed CV/DF shock therapies. ICD 14 is coupled to an extra-cardiovascular lead, such as lead 16 carrying extra-cardiovascular electrodes 24A, 24B, 28A, 28B and 30, for delivering pacing therapies, CV/DF shock therapies and sensing cardiac electrical signals.

ICD 14 includes a control module 80, memory 82, therapy delivery module 84, electrical sensing module 86, and telemetry module 88. ICD 14 may include an impedance measurement module 90 for delivering a drive signal across a therapy delivery electrode vector and measuring a resulting voltage for determining an electrical impedance of the electrode vector.

A power source 98 provides power to the circuitry of ICD 14, including each of the modules 80, 82, 84, 86, 88, 90 as needed. Power source 98 may include one or more energy storage devices, such as one or more rechargeable or non-rechargeable batteries. The connections between power source 98 and each of the other modules 80, 82, 84, 86 and 88 are to be understood from the general block diagram of FIG. 3, but are not shown for the sake of clarity. For example, power source 98 is coupled to low voltage (LV) and high voltage (HV) charging circuits included in therapy delivery module 84 for charging LV and HV capacitors, respectively, or other energy storage devices included in therapy delivery module 84 for producing electrical stimulation pulses.

The functional blocks shown in FIG. 5 represent functionality included in ICD 14 and may include any discrete and/or integrated electronic circuit components that implement analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14 or those ICD modules. The non-transitory computer-readable media storing the instructions may include any of the media listed above.

Depiction of different features as modules is intended to highlight different functional aspects and does not necessarily imply that such modules must be realized by separate hardware or software components. Rather, functionality associated with one or more modules may be performed by separate hardware, firmware or software components, or integrated within common hardware, firmware or software components. For example, cardiac pacing operations may be performed by therapy delivery module 84 under the control of control module 80 and may include operations implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24A, 24B, 28A, 28B, and 30 carried by lead 16 shown in FIGS. 1A and 1B (or electrodes 24A', 24B', 28A' and 28B' shown in FIG. 4) and the housing 15, which may function as a common or ground electrode or as an active can electrode for delivering CV/DF shock pulses.

Electrical sensing module 86 may be selectively coupled to electrodes 28A, 28B, 30 and housing 15 in order to monitor electrical activity of the patient's heart. Electrical sensing module 86 may additionally be selectively coupled to electrodes 24A and/or 24B. Sensing module 86 may include switching circuitry for selecting which of electrodes 24A, 24B, 28A, 28B, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A, 28B, 30 and housing 15. Each sensing channel may be configured to amplify, filter and rectify the cardiac electrical signal received from selected electrodes coupled to the respective sensing channel to improve the signal quality for sensing cardiac events, e.g., P-waves and/or R-waves. Each sensing channel includes cardiac event detection circuitry for sensing cardiac events from the received cardiac electrical signal developed across the selected sensing electrode vector(s). For example, each sensing channel in sensing module 86 may include an input or pre-filter and amplifier for receiving a cardiac electrical signal from a respective sensing vector, an analog-to-digital converter, a post-amplifier and filter, a rectifier to produce a digitized, rectified and amplified cardiac electrical signal that is passed to a cardiac event detector included in sensing module 86 and/or to control module 80.

The cardiac event detector may include a sense amplifier, comparator or other circuitry for comparing the rectified cardiac electrical signal to a cardiac event sensing threshold, such as an R-wave sensing threshold, which may be an auto-adjusting threshold. Sensing module 84 may produce a sensed cardiac event signal in response to a sensing threshold crossing. The sensed cardiac events, e.g., R-waves, are used for detecting cardiac rhythms and determining a need for therapy by control module 80. In some examples, cardiac electrical signals such as sensed R-waves are used to detect capture of a pacing pulse delivered by ICD 14.

Therapy delivery module 84 may include a low voltage (LV) therapy module 85 for delivering low voltage pacing pulses using an extra-cardiovascular pacing electrode vector selected from electrodes 24A, 24B, 28A, 28B, 30 and 15. LV therapy module 85 may be configured to deliver low voltage pacing pulses, e.g., 8 V or less or 10 V or less. One or more capacitors included in the LV therapy module 85 are charged to a voltage according to a programmed pacing pulse amplitude by a LV charging circuit, which may include a state machine. The LV charging circuit may charge the capacitors to a multiple of the voltage of a battery included in power source 98 without requiring a transformer. At an appropriate time, the LV therapy module 85 couples the capacitor(s) to a pacing electrode vector to deliver a pacing pulse to the heart 26.

High voltage (HV) therapy module 83 includes one or more high voltage capacitors. When a shockable rhythm is detected, the HV capacitor(s) is(are) charged to a shock voltage amplitude by a HV charging circuit according to the programmed shock energy. The HV charging circuit may include a transformer and be a processor-controlled charging circuit that is controlled by control module 80. Control module 80 applies a signal to trigger discharge of the HV capacitor(s) upon detecting a feedback signal from therapy delivery module 84 that the HV capacitors have reached the shock voltage amplitude required to deliver the programmed shock energy. In this way, control module 80 controls operation of the high voltage therapy module 83 to deliver CV/DF shocks using defibrillation electrodes 24A, 24B and/or housing 15.

HV therapy module 83 may be used to deliver cardiac pacing pulses. In this case, the HV capacitor(s) is(are) charged to a much lower voltage than that used for delivering shock therapies but may be higher than the maximum available pulse voltage amplitude produced by the LV therapy module 85. For example, the HV capacitor may be charged to 40 V or less, 30 V or less, or 20 V or less for producing extra-cardiovascular pacing pulses.

Compared to pacing pulses delivered by LV therapy module 85, pulses delivered by HV therapy module 83 may have a higher voltage amplitude and relatively longer pulse width for delivering higher energy pacing pulses for capturing the heart. More current may be delivered using a low impedance pacing electrode vector, e.g., between electrodes 24A and 24B or 24A' and 24B'. Longer pulse width is attainable due to a higher capacitance (and consequently higher RC time constant) of the HV capacitor(s). The LV therapy module 85 may be capable of producing a maximum pulse voltage amplitude of up to and including 10 V. The maximum single-pulse pacing pulse width produced by LV therapy module 85 may be 2 ms. In some examples, LV therapy module 85 may be configured to produce composite pacing pulses comprising two or more individual pulses fused in time to deliver a cumulative composite pacing pulse energy that captures the heart. Techniques for delivering composite pacing pulses are generally disclosed in the above-incorporated U.S. patent application Ser. No. 15/367,516, now issued as U.S. Pat. No. 10,080,905 (Anderson, et al.), and in provisional U.S. Pat. Application No. 62/262,412 and corresponding U.S. patent application Ser. No. 15/368,197, now issued as U.S. Pat. No. 10,449,362 (Anderson, et al.), both incorporated herein by reference in their entirety. The maximum composite pacing pulse width may be up to 8 ms or higher.

The HV therapy module 83 may be capable of producing a pulse voltage amplitude of 10 V or more and may produce mono- or multi-phasic pulses having a relatively longer pacing pulse width, e.g., 10 ms or more, because of the higher capacitance of high voltage capacitors included in HV therapy module 83. A typical HV pacing pulse width may be 10 ms; however an example range of available pulse widths may be 2 ms to 20 ms. An example of a maximum voltage amplitude that may be used for delivering high voltage pacing pulses may be 40 V. When a relatively higher pacing pulse voltage amplitude is tolerable by the patient, e.g., more than 10 V, a relatively shorter pacing pulse width, e.g., 2 to 5 ms, may be used during the high-voltage pacing output configuration. However, a longer pacing pulse width may be used as needed, e.g., a 10 V, 20 ms pacing pulse.

For the sake of comparison, the HV capacitor(s) of the HV therapy module 83 may be charged to an effective voltage greater than 100 V for delivering a cardioversion/defibrillation shock. For example, two or three HV capacitors may be provided in series having an effective capacitance of 148 to 155 microfarads in HV therapy module 83. These series capacitors may be charged to develop 100 to 800 V for the series combination in order to deliver shocks having a pulse energy of 5 Joules or more, and more typically 20 Joules or more.

In contrast, pacing pulses delivered by the HV therapy module 83 may have a pulse energy less than 1 Joule and even in the milliJoule range or tenths of milliJoules range depending on the pacing electrode impedance. For instance, a pacing pulse generated by HV therapy module 83 having a 10 V amplitude and 20 ms pulse width delivered using a pacing electrode vector between defibrillation electrodes 24A and 24B, having an impedance in the range of 20 to 200 ohms, may have a delivered energy of 5 to 7 milliJoules. When a relatively shorter pulse width is used, e.g., down to 2 ms, the pacing pulse delivered by HV therapy module 83 using defibrillation electrodes 24A and 24B (or 24A' and 24B') may be as low as 1 milliJoule. Charge balanced pacing pulses delivered by HV therapy module 83 are expected to have a pacing voltage amplitude that is less than 100 V, and typically not more than 40 V, and deliver at least 1 milliJoule but less than 1 Joule of energy. The delivered energy for a given pacing voltage amplitude will vary depending on the pulse width and pacing electrode vector impedance.

If a pace/sense electrode 28A, 28B or 30 is included in the pacing electrode vector, resulting in a relatively higher impedance, e.g., in the 400 to 1000 ohm range, the pacing pulse energy delivered may be in the range of 2 to 5 milliJoules. HV therapy module 83 may deliver more current via a lower impedance pacing electrode vector, e.g., between defibrillation electrodes 24A and 24B or 24A' and 24B', than the current delivered by LV therapy module 85 via a pacing electrode vector including a pace/sense electrode 28A, 28B or 30 (relatively higher impedance) even when the pacing voltage amplitude is the same.

Composite pacing pulses, delivered by the LV therapy module 85, having an 8 V amplitude and 8 ms pulse width may be in the range of 0.5 to 1.3 milliJoules for the range of pacing loads given in the preceding example. Extra-cardiovascular, single-pulse pacing pulses delivered by LV therapy module 83 that are 8V in amplitude and 2 ms in pulse width may be in the range of 0.2 to 0.3 milliJoules for pacing loads of 400 to 1000 ohms. In contrast, pacing pulses delivered using endocardial electrodes or epicardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms.

As will be described below, control module 80 may control HV therapy module 83 to deliver charge balanced cardiac pacing. In some examples, HV therapy module 83 is enabled to deliver cardiac pacing pulses by applying at least a minimum electrical current required to maintain switches included in HV therapy module 83 in a closed state as needed for coupling the HV capacitor(s) to a pacing electrode vector. Circuitry included in HV therapy module 83 is described in conjunction with FIG. 6 below.

In some instances, control module 80 may control impedance measurement module 90 to determine the impedance of a pacing electrode vector. Impedance measurement module 90 may be electrically coupled to the available electrodes 24A, 24B, 28A, 28B, 30 and housing 15 for performing impedance measurements of one or more candidate pacing electrode vectors. Control module 80 may control impedance measurement module 90 to perform impedance measurements by passing a signal to impedance measurement module 90 to initiate an impedance measurement of a pacing electrode vector. Impedance measurement module 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control module 80.

Control module 80 may use impedance measurements from impedance measurement module 90 to control the delivery of charge balanced pacing pulses. For instance, a pacing load impedance measurement may be used to set a variable shunt resistance included in HV therapy module 83 when a high-voltage pacing output configuration is selected for delivering extra-cardiovascular pacing pulses to heart 26. The variable shunt resistance may be coupled in parallel to the pacing load for pacing pulse delivery and set to maintain electrical current through HV therapy module switching circuitry throughout the duration of a pacing pulse delivered by the HV therapy module 83 thereby promoting an appropriate voltage signal across the pacing load for capturing the patient's heart.

Control parameters utilized by control module 80 for detecting cardiac rhythms and delivering electrical stimulation therapies and tachyarrhythmia induction pulses may be programmed into memory 82 via telemetry module 88. Telemetry module 88 includes a transceiver and antenna for communicating with external device 40 (shown in FIG. 1A) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

Figure 6:
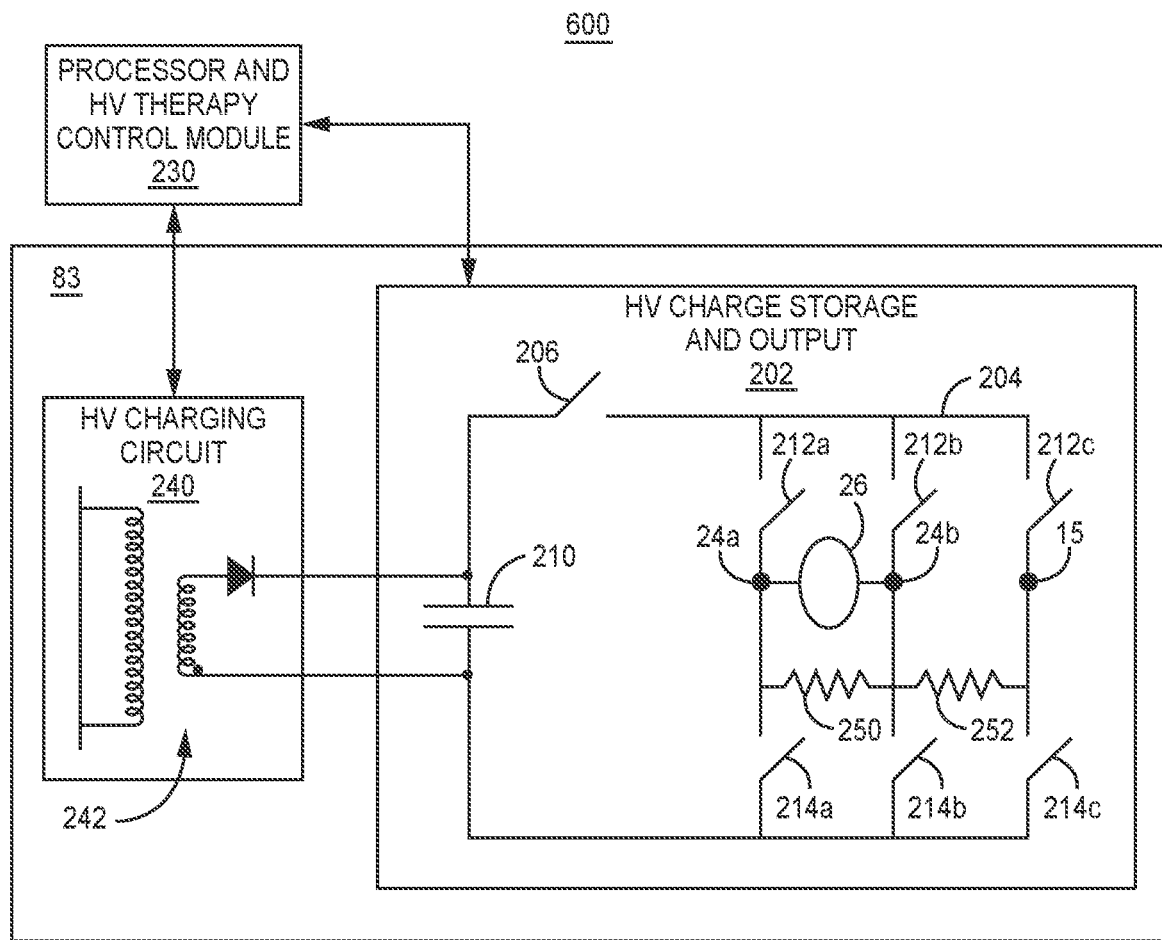
FIG. 6 is schematic diagram of HV therapy module coupled to a processor and HV therapy control module.

FIG. 6 is schematic diagram 200 of HV therapy module 83 coupled to a processor and HV therapy control module 230. HV therapy module 83 includes a HV charging circuit 240 and a HV charge storage and output module 202. Processor and HV therapy control module 230 may be included in control module 80 for controlling HV charging circuit 240 and HV charge storage and output module 202.

HV charge storage and output module 202 includes a HV capacitor 210 coupled to switching circuitry 204 via a pulse control switch 206 for electrically coupling the HV capacitor 210 to electrodes 24a, 24b and/or housing 15 to deliver a desired HV electrical stimulation pulse to the patient's heart 26. HV capacitor 210 is shown as a single capacitor, but it is recognized that a bank of two or more capacitors or other energy storage devices may be used to store energy for producing electrical signals delivered to heart 26. In one example, HV capacitor 210 is a series of three capacitors having an effective capacitance of 148 microfarads, 155 microfarads, or other selected capacitance. In contrast, holding capacitors that are included in LV therapy module 85 that are charged to a multiple of the battery voltage by a state machine may have a capacitance of up to 6 microfarads, up to 10 microfarads, up to 20 microfarads or other selected capacitance, but all have a capacitance significantly less than the effective capacitance of HV capacitor 210. The LV therapy module 85 has a lower breakdown voltage than the HV therapy module 83, allowing the HV capacitor 210 to be charged to the shock voltage amplitude, e.g., 100 V or more, required for delivering CV/DF shocks.

Switching circuitry 204 may be in the form of an H-bridge including switches 212a-212c and 214a-214c that are controlled by signals from processor and HV control module 230. Switches 212a-212c and 214a-214c may be implemented as silicon-controlled rectifiers (SCRs), insulated-gate bipolar transistors (IGBTs), metal-oxide-semiconductor field-effect transistors (MOSFETs), and/or other switching circuit components or combinations thereof.

When control module 80 determines that delivery of an electrical stimulation pulse from HV therapy module 83 is needed, switching circuitry 204 is controlled by signals from processor and HV therapy control module 230 to electrically couple HV capacitor 210 to a therapy delivery vector to discharge capacitor 210 across the vector selected from electrodes 24A, 24B and/or housing 15. The selected electrodes 24A, 24B and/or housing 15 are coupled to HV capacitor 210 by opening (i.e., turning off or disabling) and closing (i.e., turning on or enabling) the appropriate switches of switching circuitry 204 to pass a desired electrical signal to the therapy delivery electrode vector. While only electrodes 24A, 24B and housing 14 are indicated as being coupled to switching circuitry 204, it is to be understood that pace/sense electrodes 28A, 28B and 30 may be coupled to switching circuitry 204 and available for use in a pacing electrode vector.

When control module 80 determines that a shock therapy is needed based on a detected heart rhythm, e.g., VT or VF, the electrical signal delivered by HV therapy module 83 may be a monophasic, biphasic or other shaped CV/DF shock pulse for terminating the ventricular tachyarrhythmia. When control module 80 determines that a pacing therapy is needed based on a detected heart rhythm or a pacing escape interval expiring, the electrical signal delivered by HV therapy module 83 may be a monophasic or biphasic pacing pulse and may be a charged-balanced pacing pulse as described below.

In some examples, when a biphasic CV/DF shock or biphasic pacing pulse is needed, one of switches 212a, 212b and 212c may be closed simultaneously with one of switches 214a, 214b and 214c without closing both of the "a," "b" or "c" switches across a given electrode 24a, 24b or housing 15, respectively, at the same time. To deliver a biphasic pulse using electrode 24A and electrode 24B, for instance, switch 212a and 214b may be closed to deliver a first phase of the biphasic pulse. Switches 212a and 214b are opened after the first phase, and switches 212b and 214a are closed to deliver the second phase of the biphasic pulse. Switches 212c and 214c remain open or disabled in this example with electrode 24B not selected or used in the therapy delivery vector. In other examples, housing 15 may be included instead of electrode 24A or electrode 24B by closing switch 214c during the first phase and closing switch 212c in the second phase of the illustrative biphasic pulse.

The first phase of a biphasic pulse may be terminated when the pulse voltage amplitude has decayed according to a programmed "tilt." Tilt is the percentage of the leading voltage amplitude that the pulse has decayed to. For example, the first phase of a biphasic pulse may be terminated at a tilt of 50%, when the pulse amplitude has decayed to 50% of the leading voltage amplitude. If the programmed tilt is 20%, the first phase is terminated when the pulse amplitude has decayed by 20%, i.e., to 80% of the leading voltage amplitude. In other examples, the first phase and second phase are terminated according to a programmed pulse width.

When control module 80 enables a high-voltage pacing output configuration, capacitor 210 is charged to a programmed pacing pulse voltage amplitude by HV charging circuit 240 under the control of processor and HV therapy control module 230. Switches 212a-212c and 214a-214c are controlled to be open or closed by processor and HV therapy control module 230 at the appropriate times for delivering a monophasic, biphasic or other desired pacing pulse by discharging capacitor 210 across the pacing load presented by heart 26 and a selected pacing electrode vector, e.g., electrodes 24A and 24B. The capacitor 210 is coupled across the selected pacing electrode vector for the programmed pacing pulse width or according to a programmed tilt.

Processor and HV therapy control 230 may control HV therapy module 83 to deliver charge balanced cardiac pacing pulses by controlling HV therapy module 83 to deliver a first pulse which may be a monophasic pulse, a biphasic pulse, or the first phase of a biphasic pulse and a second pulse following the first pulse so that the first pulse and the second pulse are charge balanced. The second pulse may be a monophasic pulse, a biphasic pulse or the second phase of a biphasic pulse. At least the first pulse captures the myocardium to pace the heart. The second pulse may or may not contribute to capturing the heart but balances the electrical charge delivered to the pacing load during the first pulse. As described below, in some instances only the first pulse captures the heart, and the second pulse is delivered to balance the charge of the first pulse. In other examples, the second pulse also contributes to pacing and capturing the heart, e.g., in the case of the first pulse and the second pulse each being monophasic pacing pulses delivered at a pacing rate interval so that each capture the heart but are delivered having opposite polarity.

Before the first pulse, the HV capacitor 210 may be charged to the programmed pacing pulse voltage amplitude. In some examples HV capacitor 210 is recharged between the first and second pulses, to generate and deliver a second pulse that balances the charge delivered during the first pulse. HV charging circuit 240 is powered by power source 98 (FIG. 5). HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV therapy control 230, which receives feedback signals from HV charge storage and output module 202 to determine when capacitor 210 is charged to a programmed voltage. A charge completion signal is passed to HV charging circuit 240 to terminate charging by processor and HV therapy control module 230. One example of a high voltage charging circuit and its operation is generally disclosed in U.S. Pat. No. 8,195,291 (Norton, et al.), incorporated herein by reference in its entirety.

HV charge storage and output module 202 is shown to include an optional shunt resistance 250 in parallel to the pacing load shown schematically as heart 26 when electrodes 24A and 24B are selected as the anode and cathode (or cathode and anode, respectively) of the pacing electrode vector. It is recognized that a shunt resistance may be provided in parallel to the pacing load for any selected pacing electrode vector, for example shunt resistance 252 is shown schematically if the pacing electrode vector includes electrode 24B and housing 15. Likewise a shunt resistance may be provided in parallel to the pacing load when the pacing electrode vector includes electrode 24A and housing 15.

Switches 212a-212c and switches 214a-214c may require a minimum current flow to hold them closed (i.e., ON or enabled) for passing current as HV capacitor 210 is discharged. The minimum current to enable (close) switches 214a-214c may be approximately 10 milliamps. The minimum current to maintain these switches in the closed state may be less than 10 milliamps, but, depending on the pacing load impedance and other conditions, the electrical current passing through enabled switches of switches 212a-212c and 214a-214c may fall below the minimum current required to keep the switches closed as capacitor 210 is discharged across a selected pacing electrode vector. If the current passing through a respective switch falls below the minimum current required to keep the switch closed, the switch may open (or become disabled) causing premature truncation of the pacing pulse, which could result in loss of capture and/or inadequate charge balancing. As such, a minimum pacing pulse voltage amplitude may be set for delivering pulses from HV therapy module 83 in order to reduce the likelihood of the electrical current produced during capacitor 210 discharge falling below the minimum current required to maintain a stable state of enabled switches of switching circuitry 204 during a programmed pacing pulse width (or until a programmed tilt has been reached).

The shunt resistance 250 or 252 may be a variable resistance that is set to match a pacing electrode vector impedance so that the load across heart 26 using a selected pacing electrode vector matches the shunt resistance. In this way, current through the switching circuitry 204 may be maintained at or above a minimum current required to maintain a stable state of enabled switches of switching circuitry 204 during the pacing pulse.

If the shunt resistance 250 or 252 is lower than the pacing electrode vector impedance, current produced by discharging capacitor 210 may be shunted away from the pacing load, e.g., the pacing electrode vector between electrodes 24a and 24b and heart 26, resulting in less energy delivered to heart 26, which may result in loss of capture. Accordingly, processor and HV therapy control module 230 may be configured to retrieve a pacing electrode vector impedance measurement from impedance measurement module 90 and set the shunt resistance 250 (or 252) to match the pacing electrode vector impedance or to a resistance that maintains a current through enabled switches of switching circuit 204 that keeps the switches on or closed. The shunt resistance may be equal to, less than or in some cases greater than the pacing load impedance but is generally adjusted to maintain adequate current through enabled switches of switching circuitry 204 to keep the appropriate switches closed for the full pulse width of each of the first and second pulses of a pair of charge balanced pulses.

In other examples, a minimum voltage charge of capacitor 210 may be set to provide the minimum current required to maintain an enabled state of selected switches of switching circuitry 204, but pacing energy may be intentionally shunted away from the pacing load including heart 26 in order to reduce the delivered pacing pulse energy. If the pacing amplitude capture threshold is below the minimum voltage amplitude required to maintain the minimum current to keep switches 212a-212c and 214a-214c on when they are enabled by processor and HV therapy control module 230, the energy delivered across the pacing electrode vector may be reduced by setting the variable shunt resistance 250 (or 252) to a value that is less than the pacing electrode vector impedance. This current shunting may reduce skeletal muscle recruitment caused by the extra-cardiovascular pacing pulse while still providing effective capture of heart 26.

Since the range of pacing load impedances and pacing voltage amplitudes may vary between patients and over time within a patient, a variable shunt resistance may be provided to enable selection of the appropriate resistance for shunting the required current through the switching circuitry 204. It is contemplated, however, that in some examples a fixed resistance shunt may be provided. For example, the resistance needed to shunt current to the switching circuitry 204 when the pacing load impedance is high may still shunt some current to the switching circuitry when the pacing load impedance is relatively lower. An optimal value for a fixed resistance shunt may be determined based on empirical data, e.g., typical pacing load impedances and pacing pulse voltage amplitudes used clinically.

The pacing electrode vector coupled to HV capacitor 210 via switching circuitry 204 may include electrodes 24a, 24b, 28a, 28b and/or 30 carried by lead 16. Housing 15 may be unused for cardiac pacing pulse delivery by holding switches 212c and 214c open. Depending on the implant location of ICD 14 and lead 16 and the resulting electrical stimulation delivery vector between the housing 15 and an electrode 24a, 24b, 28a, 28b or 30, greater recruitment of skeletal muscle may occur when housing 15 is included in the pacing electrode vector. A larger volume of skeletal muscle tissue may lie along a vector extending between the distal portion 25 of lead 16 and housing 15 than along a vector extending between the two electrodes carried by lead distal portion 25. In the example configurations of FIGS. 1A-2C, for example, a pacing pulse may be delivered between electrodes 24A and 24B, between electrodes 28A and 28B, between electrodes 28A and 24A or between electrodes 28B and 24B to limit skeletal muscle recruitment compared to a pacing electrode vector that includes housing 15. In other electrode configurations and implant locations, the electrodes used to deliver extra-cardiovascular pacing pulses by HV therapy module 83 may be selected to provide a pacing electrode vector that minimizes the volume of skeletal muscle included in the pacing electrode vector while directing sufficient energy to the heart 26 for capturing and pacing the heart.

Figure 7:
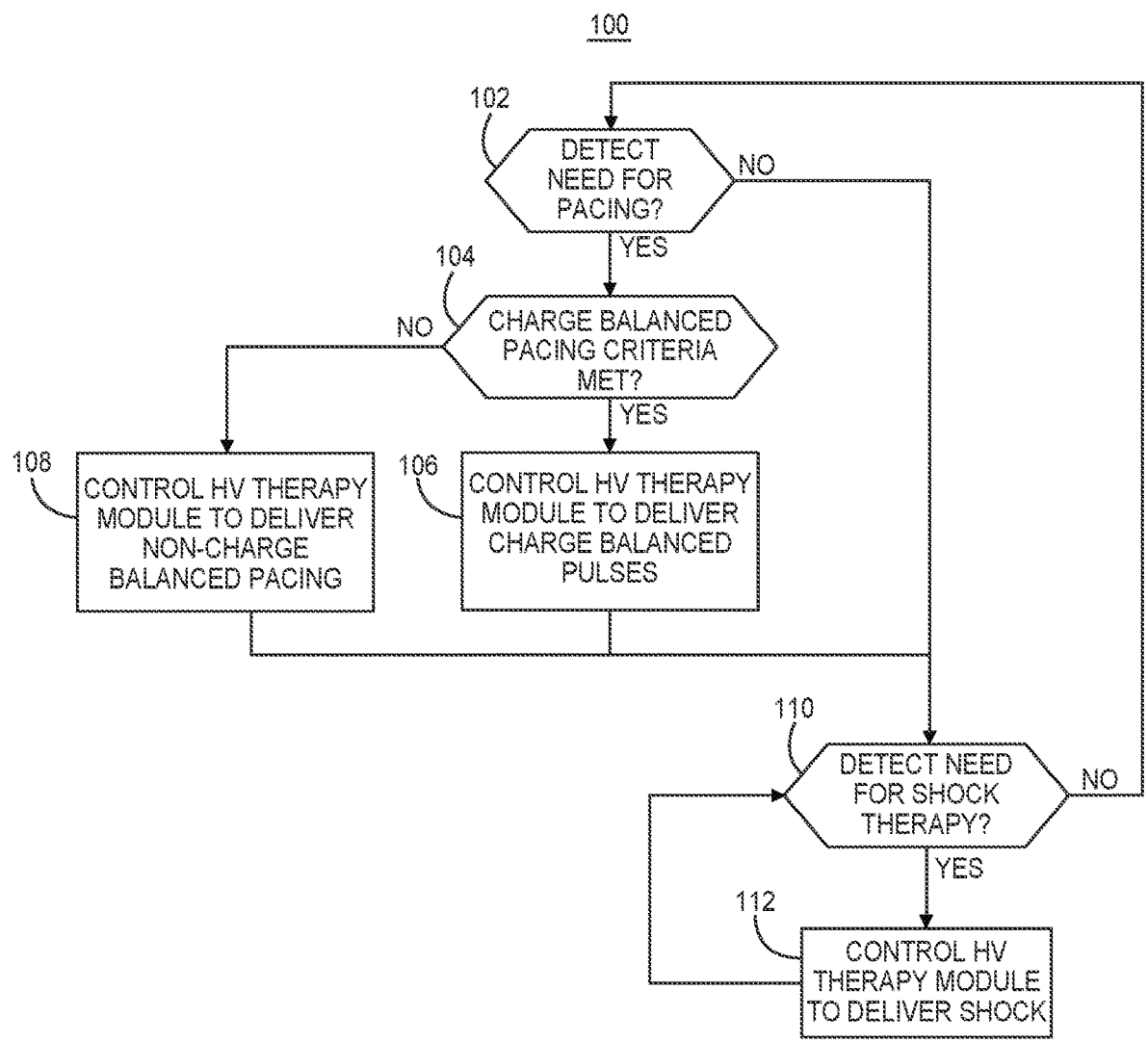
FIG. 7 is a flow chart of a method for controlling a HV therapy delivery module for delivering cardiac electrical stimulation therapies according to one example.

FIG. 7 is a flow chart 100 of a method for controlling therapy delivery module 83 for delivering cardiac electrical stimulation therapies according to one example. At block 102, control module 80 determines if there is a need for delivering cardiac pacing. For instance, a bradycardia pacing pulse may be required when the intrinsic heart rate is below a programmed lower pacing rate or a temporary pacing rate automatically set by control module 80 according to a rate-responsive sensor indicated pacing rate. ATP may be required when a ventricular tachycardia is detected. In some cases, pacing is required during post-shock recovery following a CV/DF shock therapy. In still other examples, a need for pacing may include pacing for tachyarrhythmia induction during ICD testing. A need for pacing may be determined in response to ICD 14 receiving a telemetry communication from external device 40 based on a user command.

Control module 80 may be configured to deliver all pacing pulses as charge balanced pacing pulses using any of the techniques described below in conjunction with FIGS. 8A-12. Alternatively, control module 80 may be configured to determine if charge balanced pacing criteria are met at block 104. If charge balanced pacing criteria are met at block 104, pacing pulses may be delivered as charge balanced pulses at block 106 according to the timing, pulse amplitude, pulse width and other pacing therapy protocol parameters. If charge balanced pacing criteria are not met, control module 80 may control the HV therapy module 83 to deliver pacing pulses that are not charge balanced at block 108.

Control module 80 may determine if charge balanced pacing criteria are met at block 104 by comparing the pacing pulse amplitude to a charge balancing threshold amplitude, comparing the pacing pulse width to a charge balancing threshold width, comparing the pacing load impedance to a charge balancing threshold impedance, comparing the pacing rate to a charge balancing threshold rate, comparing the scheduled pacing therapy or programmed pacing mode to charge balancing pacing therapy criteria, and/or comparing the number of previously-delivered pacing pulses to a charge balancing threshold pulse number. Control module 80 may be configured to control HV therapy module 83 to deliver pacing pulses that are non-charge balanced pulses, e.g., non-charge balanced monophasic or biphasic pulses, unless charge balanced pacing criteria are met. If charge balancing criteria are met, the control module 80 switches to controlling HV therapy module 83 to delivering charge-balanced pacing pulses.

In one example, the charge balanced pacing criteria applied at block 104 requires a threshold number of previously-delivered non-charge balanced pacing pulses delivered by ICD 14. Control module 80 may be configured to count the number of non-charge balanced pacing pulses delivered to the patient, e.g., since the time of implant of ICD system 10 or at least since the time of implantation of the lead 16 carrying at least one electrode used in the pacing electrode vector. If the number of non-charge balanced pacing pulses delivered reaches a charge balancing threshold, e.g., 1,000 pacing pulses, control module 80 switches to controlling HV therapy module 83 to deliver charge balanced pacing pulses for the remaining implant life of lead 16 or ICD 14. Some patients may require only infrequent pacing which may not lead to significant electrode corrosion or sensing issues. As such, a limited number of non-charge balanced pacing pulses over the lifetime of the implanted ICD system 10 may be delivered before requiring charge balancing of delivered pacing pulses. The limited number of pacing pulses delivered as non-charge balanced pacing pulses may include pulses delivered during a specified therapy, e.g., during a bradycardia pacing, or during all pacing therapies and modalities, including pulses delivered to induce VT or VF in some examples.

When more than one pacing electrode vector is available, the number of non-charge balanced pacing pulse pulses may be counted for a given pacing electrode vector. If the number of non-charge balanced pacing pulses for a first pacing electrode vector is reached, at block 104 but another acceptable pacing electrode vector is available, control module 80 may determine that charge balanced pacing criteria are not met at block 104. Control module 80 may control therapy delivery module 84 to switch the pacing electrode vector coupled to HV therapy module 83 to a second pacing electrode vector that includes at least one electrode not included in the first pacing electrode vector. In that way, corrosion may be avoided without converting to charge balanced pacing. Non-charge balanced pacing may continue to be delivered at block 108.

If the non-charge balanced pacing pulses delivered using the second pacing electrode vector is reached, or if no other acceptable pacing electrode vector (e.g., having acceptable pacing capture threshold) is available, the charge balanced pacing criteria are met at block 104 and control module 80 may control HV therapy module 83 to deliver charge balanced pacing pulses using a selected pacing electrode vector, which may be the first or second pacing electrode vector, at block 106. In some examples, a pacing electrode vector having a relatively lower capture threshold and/or relatively higher impedance may be selected at block 106 for delivery of charge balanced pacing pulses.

As mentioned above, pacing load impedance may be compared to a threshold. If the impedance is less than a charge balancing impedance threshold, charge balancing may be desired. The pacing electrode vector between electrodes 24A and 24B may be expected to be between 20 and 200 ohms. An example impedance threshold for requiring charge balanced pacing pulses may be 50 ohms. In other examples, if the programmed pulse amplitude is greater than a threshold amplitude and/or the pulse width is greater than a threshold width, the relatively high pulse energy being delivered to capture the heart may warrant charge balancing. An example of a threshold amplitude may be 15 Volts and an example of a threshold width may be 10 ms, though these examples are illustrative in nature and other respective amplitude and pulse width thresholds may be used. In some examples, a combination of the number of previously delivered non-charge balanced pacing pulses, pulse voltage amplitude, pulse width and/or pacing load impedance may be compared to charge balance pacing criteria at block 104. In yet another example, a determination of the accumulated delivered pacing pulse energy over the life of the ICD system 10 based on individual pacing pulse energy and the total number of pacing pulses delivered may be compared to criteria for determining if charge balanced pacing criteria are met at block 104.

In some examples, charge balanced pulses may be delivered when the needed pacing therapy is expected to result in relatively frequent or sustained pacing, and non-charge balanced pacing pulses may be delivered when the pacing therapy is expected to require in relative few pacing pulses and infrequent pacing. For example, post-shock pacing pulses for treating post-shock asystole may be delivered using non-charge balanced pacing. Shock delivery is expected to be relatively infrequent in most patients, and post-shock pacing may last one minute or less resulting in relatively few pacing pulses being delivered. In other examples, control module 80 may control HV therapy module 83 to deliver ATP or tachyarrhythmia induction pulses by delivering non-charge balanced pacing pulses since a limited number of pulses, e.g., 8 to 12 pulses, are delivered in a burst of ATP pulses or a burst of tachyarrhythmia induction pulses. ATP pulses may be delivered as non-charge balanced monophasic or biphasic pulses, according to the ATP protocol. Techniques for delivering tachyarrhythmia induction pulses by HV therapy module 83 are disclosed in provisionally-filed U.S. Patent Application No. 62/262,500 and corresponding pending U.S. patent application Ser. No. 15/367,448, now issued as U.S. Pat. No. 10,046,168 (Nikolski, et al.), both incorporated herein by reference in their entirety.

If a bradycardia pacing mode is programmed to be VVI in a patient with only occasional atrioventricular conduction issues, control module 80 may control HV therapy module to deliver non-charge balanced pacing at block 108. In this case, the pacing burden may be monitored and when the daily pacing burden remains below a threshold number of pacing pulses or percentage of time, non-charge balanced pacing may be delivered.

If bradycardia pacing is being delivered in a VVI or VOO pacing mode in a patient that is pacing dependent some or all of the time, however, control module 80 may control HV therapy module 83 to deliver charge balanced pacing pulses at block 106. Cardiac pacing may be required frequently and over sustained time intervals. As such, the type of pacing therapy and pacing mode may be criteria applied at block 104 for determining whether to deliver charge balanced pacing pulses. Pacing therapy and mode criteria applied at block 104 may require charge balanced pacing pulses for all bradycardia pacing modes and allow non-charge balanced pacing for ATP, post-shock pacing and tachyarrhythmia induction pacing. In another example, the therapy and mode criteria applied at block 104 may require charge balanced pacing pulses only for VOO and rate responsive pacing modes and allow non-charge balanced pacing for ATP, post-shock pacing and VVI bradycardia pacing without rate response. The pacing therapy and mode criteria applied at block 104 may be user programmable to tailor the criteria according to individual patient pacing needs.

The example criteria described in the foregoing may be used in various combinations. For example, the charge balanced pacing criteria applied at block 104 may allow non-charge balanced pacing to be delivered for specified pacing therapies or modes and require charge balanced pacing for other specified pacing therapies and modes after the number of non-charge balanced pacing pulses delivered for all therapies reach a maximum threshold number of non-charge balanced pacing. In other cases, all pacing pulses are delivered using charge balancing techniques after a threshold number of non-charge balanced pacing pulses.

In addition to monitoring for a need for pacing therapy, control module 80 monitors the heart rhythm for a need for shock therapy at block 110. When a shock therapy is required, e.g., upon detecting VT (not terminated or treatable by ATP) or VF, the control module 80 controls HV therapy module 83 to withhold and pacing pulses being delivered or scheduled to be delivered at blocks 106 or 108 and deliver a CV/DF shock at block 112. The HV capacitor 210 of HV therapy module is charged to a programmed pacing voltage amplitude at blocks 108 and 106 for delivering non-charge balanced and charge balanced pacing pulses. The HV capacitor 210 is charged to a shock voltage amplitude according to a programmed CV/DF shock energy at block 112. As such, control module 80 is configured to control HV therapy module 83 to deliver high voltage CV/DF shocks and cardiac pacing pulses, which may be charge balanced cardiac pacing pulses but may include non-charge balanced cardiac pacing pulses under some conditions (as determined at block 104).

After delivering a shock at block 112, the control module 80 may determine if the tachyarrhythmia has been terminated or if another shock is required by returning to block 110. When a shockable rhythm is not being detected, "no" branch of block 110, control module 80 continues monitoring for a need for a pacing therapy as indicated at block 102.

Figure 8A:
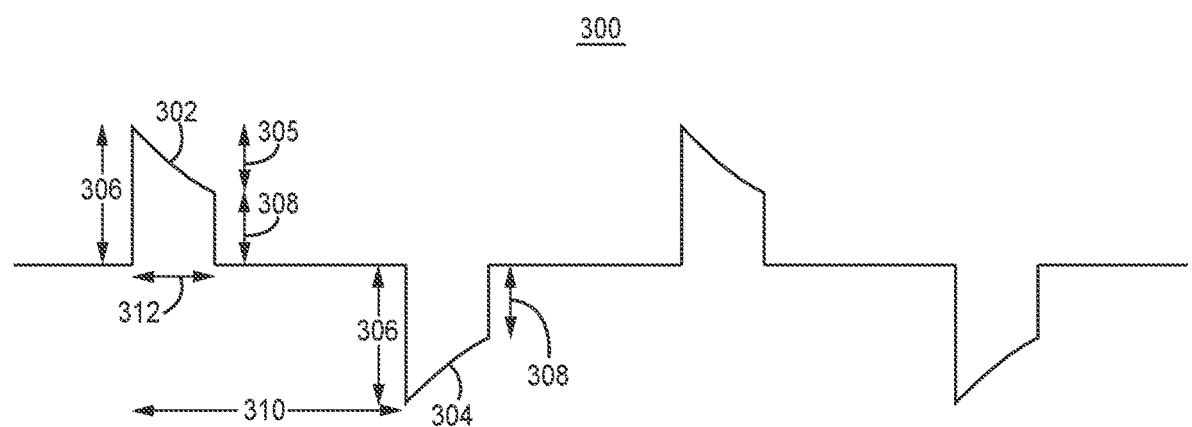
FIGS. 8A and 8B are timing diagrams of charge balanced pacing pulses that may be delivered by the HV therapy module of FIG. 6.

FIG. 8A is a diagram 300 of charge balanced pacing pulses that may be delivered by HV therapy module 83 at block 106 of FIG. 7 under the control of control module 80 according to one example. In this example, a first pulse 302 and a second pulse 304 are each delivered as a monophasic pacing pulse. Pulse 302 and pulse 304 are delivered having opposite polarity to provide charge balancing of the first pulse 302 by the second pulse 304. Prior to each pulse 302 and 304, HV capacitor 210 is charged to a programmed pulse voltage amplitude corresponding to the leading voltage amplitude 306 of each pulse 302 and 304.

The first pulse 302 is shown having a positive polarity. The first pulse 302 is delivered using a selected pacing electrode vector, e.g., between electrodes 24A and 24B of FIG. 1A or between electrodes 24A' and 24B' of FIG. 4. A first electrode of the pacing electrode vector is used as the cathode electrode, and the second electrode of the pacing electrode vector used as the return anode. For instance, if the selected pacing electrode vector is the vector between electrode 24A' and 24B' of FIG. 4, switching circuitry 204 may be controlled by processor and HV therapy control 230 to couple electrode 24A' to the HV charge storage and output module 202 as the cathode electrode for discharging HV capacitor 210 for a pacing pulse width 312. The pacing pulse width 312 may be controlled by setting a counter or timer for controlling pulse control switch 206 of HV therapy module 83 (shown in FIG. 6).

The switching circuitry 204 may be uncoupled from HV capacitor 210 after the programmed pacing pulse width 312. In other examples, the pulse width 312 may be controlled by a programmed tilt 305. For example, the first pulse 302 may be terminated according to a tilt 305 set to 50%. When the decaying voltage amplitude of pulse 302 reaches a voltage 308 equal to 50% of the leading voltage amplitude 306, the first pacing pulse 302 is terminated. Switching circuitry 204 may be disabled to uncouple the pacing electrode vector from the HV capacitor 210 or pulse control switch 206 is opened.

The second pulse 304 is a pacing pulse intended to capture the heart and is delivered at a pacing interval 310 according to the particular pacing therapy protocol or pacing mode. Pacing interval 310 may be a lower rate interval e.g., during VVI(R) or VOO(R) pacing, an ATP interval during ATP therapy, or a back-up pacing interval during post-shock pacing. In some instance, pacing interval 310 may be an interval between tachyarrhythmia induction pulses.

The second pulse 304 is delivered having opposite polarity as the first pulse 302. Continuing the example given above, if the selected pacing electrode vector is the vector between electrode 24A' and 24B' of FIG. 4, switching circuitry 204 is controlled by processor and HV therapy control 230 to couple electrode 24B' to the HV charge storage and output module 202 as the cathode electrode for discharging HV capacitor 210 for delivery of the negative polarity second pulse 304. Electrode 24A' is the return anode.

The second pulse 304 is delivered having the same leading voltage amplitude 306 and trailing voltage amplitude 308 as the first pulse 302. The processor and HV therapy control 230 controls HV charging circuit 240 to recharge the HV capacitor 210 to the programmed pacing pulse voltage amplitude defining leading pulse voltage 306 during the pacing interval 310. Processor and HV therapy control 230 terminates the second pulse 304 according to the pulse width 312 or according to the programmed tilt 305, e.g., 50%. In this way, the second pulse 304 delivers approximately the same energy as the first pulse 302. The net charge applied across the pacing load is balanced between the two pulses 302 and 304.

Figure 8B:
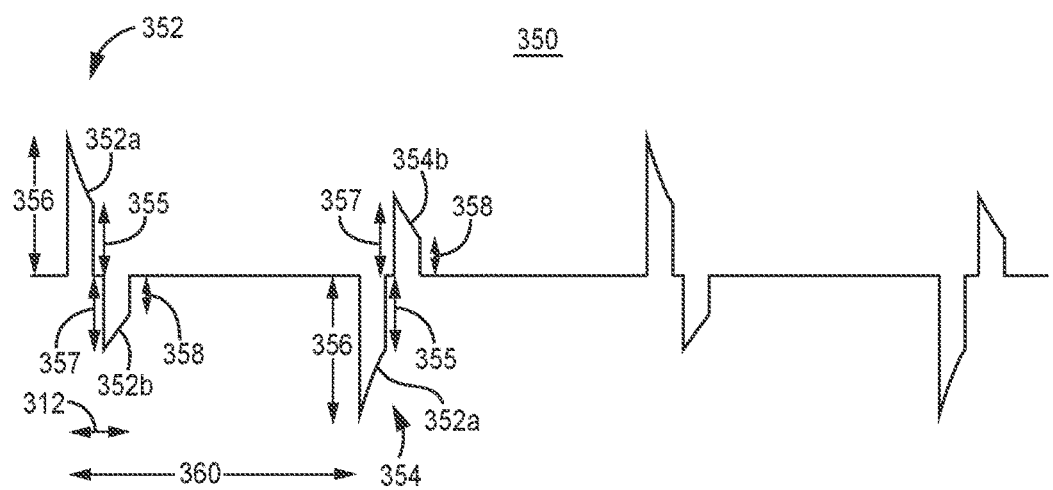

FIG. 8B is a diagram 350 of biphasic pacing pulses delivered during charge balanced pacing at block 106 of FIG. 7 according to another example. The first and second pulses 302 and 304 of FIG. 8A are monophasic pulses. Switching of circuitry 204 occurs at the onset and termination of the first pulse 302 and the second pulse 304 but not during the first pulse 302 or the second pulse 304. Switching of circuitry 204 occurs during the pacing pulse interval 310, between pulses 302 and 304, to switch the polarity of the delivered monophasic pulses 302 and 304. Charge balanced pacing that includes delivering alternating polarity pacing pulses, however, may include switching during each of the first and second pulses to deliver biphasic pacing pulses instead of monophasic pacing pulses.

In FIG. 8B, the first pacing pulse 352 and the second pacing pulse 354 are both biphasic pacing pulses. First pulse 352 has a leading voltage amplitude 356 of a first phase 352a and a leading voltage amplitude 357 of second phase 352b. The trailing voltage amplitude 355 of first phase 352a is approximately equal to the leading voltage amplitude 357 (though a slight increase in voltage amplitude may occur due to capacitor recovery during switching). When the decaying amplitude of the first phase 352a reaches a voltage 355 according to a programmed tilt or a programmed pulse width for the first phase 352a, the first phase 352a is terminated and the second phase 352b is started by controlling switching circuitry 204 to reverse the polarity of the cathode and anode electrodes of the pacing electrode vector. The second phase 352b may be terminated upon a programmed pacing pulse width 312. In other examples, the second phase 352b may be terminated according to a programmed tilt, e.g., when the trailing voltage amplitude 358 reaches 1-tilt times the leading voltage amplitude 357 of the second phase 352b. Pulse 352 is a biphasic pulse but is not balanced since the charge delivered during the first phase 352a is generally higher and not balanced by the charge delivered by the second phase 352b.

In order to reduce the effects of the first pulse 352 on electrode corrosion over time, the second pulse 354 is delivered as a biphasic pulse having a first phase 354a that is opposite in polarity from the first phase 352a of the first pulse 352 and a second phase 354b that is opposite in polarity from the second phase 352b of the first pulse 352. The first phase 354a and second phase 354b of second pulse 354 may be delivered by controlling switching circuitry 204 to switch the polarity of the pacing electrode vector when the pulse voltage amplitude has reached a voltage according to the programmed tilt used to switch phases of the first pulse 352. The leading amplitude 356 and trailing amplitude 358 are controlled to be approximately equal (within electronics specification) in the first and second pulses 352 and 354. Likewise the trailing amplitude 355 of the first phases 352a and 354a, which is approximately equal to the leading amplitude 357 of the second phases 354a and 354b, is approximately equal and controlled according to a programmed tilt at which the switching circuitry 204 is controlled to switch the polarity of the electrodes of the pacing electrode vector. Alternatively, the first and second phases of the second pulse 354 may be controlled according to a programmed pulse width.

Since the charge delivered during the first phase 352a is balanced by the charge delivered during the first phase 354a and the charge delivered in the second phase 352b is balanced by the charge delivered in the second phase 354b, the alternating polarity biphasic pacing pulses 352 and 354 provide charge balanced pacing from the HV therapy module 83. In order to optimize charge balancing when alternating polarity pulses are used as shown in FIGS. 8A and 8B, an even number of pacing pulses may be delivered. In some instances, however, it is recognized that an odd number of pulses may be delivered resulting in a final pulse that is not charge balanced by a subsequent pacing pulse.

Figure 9A:
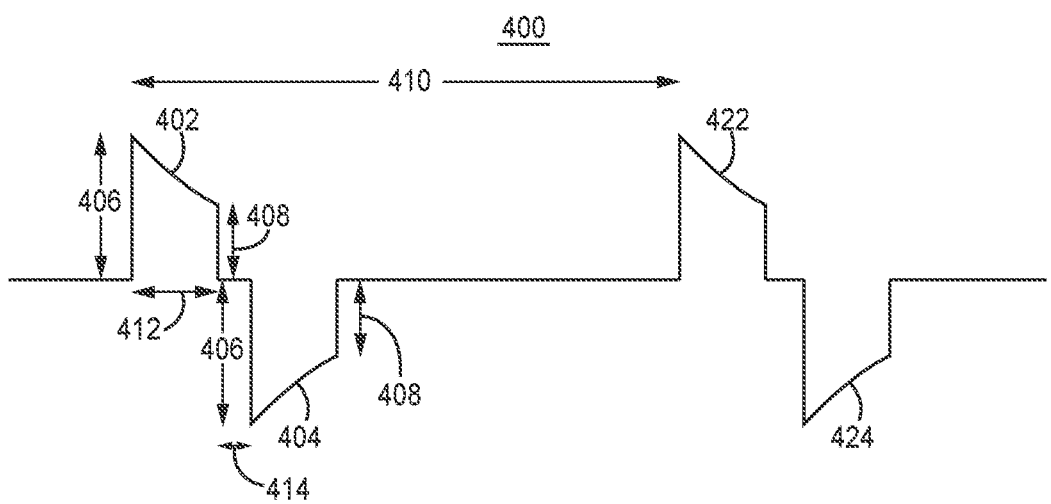
FIGS. 9A and 9B are timing diagrams of an alternative charge balanced pacing technique that may be performed by the HV therapy module of an extra-cardiovascular ICD.

FIG. 9A is a diagram 400 of an alternative charge balanced pacing technique that may be performed by ICD 14 at block 106 of FIG. 7. In this example, a first pulse 402 is delivered as a monophasic pacing pulse intended to capture the patient's heart and cause an evoked response (depolarization). First pulse 402 has a leading voltage amplitude 406 corresponding to a programmed pacing voltage amplitude and is terminated upon reaching a trailing voltage amplitude 408 according to a programmed tilt. Alternatively, the first pulse 402 may be controlled to have a programmed pacing pulse width 412 such that the total delivered energy is greater than a capture threshold of the patient's heart.

A second pulse 404 having leading voltage amplitude 406 is delivered at a very short interpulse time interval 414, so that the second pulse 404 occurs after depolarization of the cardiac tissue caused by the first pulse 402 and during the physiological refractory period of the myocardium. The HV capacitor 210 is recharged to the pacing voltage amplitude corresponding to leading voltage amplitude 406 during interpulse interval 414. Interpulse interval 414 may be 10 to 30 ms for example. The time required to recharge the HV capacitor 210 to the pacing voltage amplitude between the first pulse 402 and the second pulse 404 is dependent on the pacing voltage amplitude, pulse width 412, and pacing load impedance and other factors. The interpulse interval 414 is kept short enough so that the second pulse 404 is not delivered after the physiological refractory period. The second pulse 404 is delivered and may be terminated prior to the vulnerable period of the heart associated with myocardial repolarization and does not contribute to capturing or pacing the patient's heart. The switching circuitry 204 is controlled by processor and HV therapy control 230 to switch the polarity of the pacing vector electrodes coupled via switching circuitry 204 to the HV capacitor 210 during the interpulse interval 414.

The second pulse 404 is delivered having the same leading voltage amplitude 406 as the first pulse 402 and the same trailing voltage amplitude 408 as the first pulse 402 but opposite polarity so that the charge delivered during the second pulse 404 balances the charge delivered during the first pulse 402. The charge delivered during the second pulse 404, however, is delivered after the first pulse 402 has caused an evoked response and is not used to pace the heart. The second pulse 404 is delivered for charge balancing without contributing to or causing an evoked response of the heart.

The next monophasic pacing pulse 422 is delivered at a pacing interval 410 following the first pulse 402. As described above, pacing interval 410 may be a lower rate interval, ATP interval, back-up pacing interval or other pacing interval used to control the rate of pacing pulses. The next pacing pulse 422 is followed by a charge balancing second pulse 424 delivered in the same manner as the charge balancing second pulse 404 described above. In this way, monophasic pacing pulses 402 and 422 are delivered at a desired pacing rate and are each followed by a charge balancing monophasic pulse delivered during myocardial refractory. An odd or even number of first pulses 402 and 422 that actually pace the heart may be delivered since each first pacing pulse 402 and 422 is followed immediately by a second, charge balancing pulse 404 and 424, respectively, so that charge balancing occurs within each pacing cycle. Each of the pulses 402, 404, 422 and 424 may be delivered having a controlled pulse width 412 or a controlled tilt and the same (absolute) leading voltage amplitude 406 so that each pair of pulses 402 and 404 and 422 and 424 are charge balanced.

Figure 9B:
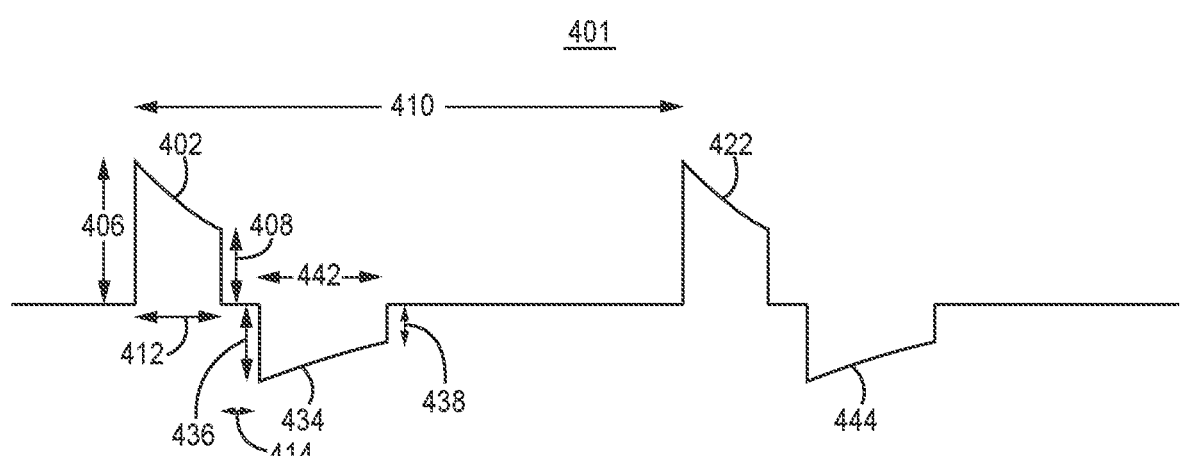

FIG. 9B is a diagram 401 of charge balanced pacing pulses that may be delivered by HV therapy module 83 according to another technique. The first pulse 402 is delivered as described above in conjunction with FIG. 9A for capturing and pacing the heart. In the example of FIG. 9B, the HV capacitor 210 is not recharged during interpulse interval 414 after the first pulse 402. The switching circuitry 204 is controlled to switch the polarity of the pacing electrode vector during interpulse interval 414 and the residual charge remaining on the HV capacitor 210 after first pulse 402 is used to deliver the second pulse 434. The second pulse 434 is delivered during the myocardial refractory period after the short interpulse interval 414, e.g., 10 ms. In this case, the interpulse interval 414 may be minimized since the HV capacitor 210 is not recharged. The leading voltage amplitude 436 may correspond to the trailing voltage amplitude 408 of the first pulse 402.

The pulse width 442 of the second pulse 434 is controlled to deliver a balanced charge during the pacing cycle. The pulse width 442 required to deliver the same energy at an opposite polarity as the first pulse 402 may be determined by control module 80 based on the measured impedance of the pacing load and the capacitance of HV capacitor 210 or the measured trailing voltage amplitude 408 of the first pulse 402.

Knowing the leading voltage amplitude 406 and the trailing voltage amplitude 408 of the first pulse 402, the energy removed from the HV capacitor 210 can be approximated. For example, the estimated energy delivered during the first pulse 402 may be estimated by control module 80 according to the following equation:

$$\text{Delivered Energy(first pulse)} = C((LPA_1)^2 - (TPA_1)^2)/2$$

where C is the effective capacitance of HV capacitor 210, $LPA_1$ is the leading voltage amplitude 406 and $TPA_1$ is the trailing voltage amplitude 408 of the first pulse 402.

The target trailing voltage amplitude 438 of the second pulse 434 may be determined by setting the delivered energy in the first pulse 402 (determined by the above equation) equal to an expression for the delivered energy in the second pulse 434 and solving for the trailing voltage amplitude 438 of the second pulse 434:

$$\text{Delivered Energy(first pulse)} = C^*((LPA_2)^2 - (TPA_2)^2)/2$$

where C is again the effective capacitance of HV capacitor 210, $LPA_2$ is the leading voltage amplitude 436 of the second pulse 434 and $TPA_2$ is the trailing voltage amplitude 438 of the second pulse 434. This equation is solved for $TPA_2$ to yield the target trailing voltage amplitude 438 that will result in a balance of the energy delivered during the first and second pulses 402 and 434.

The trailing voltage amplitude 438 computed using the above equation may be used by control module 80 to control the delivery of the second pulse 434 by monitoring the second pulse voltage amplitude during capacitor discharge and terminating the second pulse 434 when the voltage amplitude reaches the trailing voltage amplitude 438. In another example, the target trailing voltage amplitude may be used for determining the appropriate tilt for controlling the termination of the second pulse 434. In yet another example, the target trailing voltage amplitude may be used for determining the appropriate pulse width 442 of second pulse 434 to reach the trailing voltage amplitude 438. In some examples, the first pulse 402 and the second pulse 434 are monophasic pulses delivered at an interpulse interval 414 during which computations or determinations may be made for determining and setting control parameters needed for delivering second pulse 434 as a charge balancing pulse.

In other examples, the two pulses 402 and 434 are first and second phases of a biphasic pulse that is controlled according to pulse control parameters stored in memory, e.g., in look-up tables, for the paired, charge balanced pulses. In one example, if pulse 402 is controlled to have a 10% tilt, i.e., trailing voltage amplitude 408 has decreased by 10% from leading voltage amplitude 406 to 90% of the leading voltage amplitude 406, second pulse 434 may be controlled to be terminated using a 12.5% tilt. Other examples of tilts of the first pulse 402 and the second pulse 434, respectively, that may be used to deliver charge balanced paired pulses 402 and 434 include 20% and 33.9%, 25% and 52.9%, 29% and 87.25%, respectively. If the tilt of the first pulse 402 is set too high, e.g., more than 29%, the remaining charge on the HV capacitor 210 may be inadequate for delivering the second charge balancing pulse 434.

Instead of controlling the termination of the second pulse 434 according to a tilt, the second pulse 434 may be terminated at a controlled pulse width 442 that may be calculated using the RC time constant of the pacing load. In some examples, the pulse width 442 of the second pulse 434 may be stored in a look up table in memory 82 for controlling the termination of second pulse 434 based on the RC time constant determined from the known capacitance of HV capacitor 210 and the impedance of the pacing load (which may be measured by impedance measurement module 90).

The next pacing pulse 422 is delivered at a pacing interval 410 in the same manner as pacing pulse 402 and is followed by a charge balancing pulse 444 having opposite polarity delivered in the same manner as charge balancing pulse 434. Charge balancing is achieved within each pacing cycle.

Figure 10:
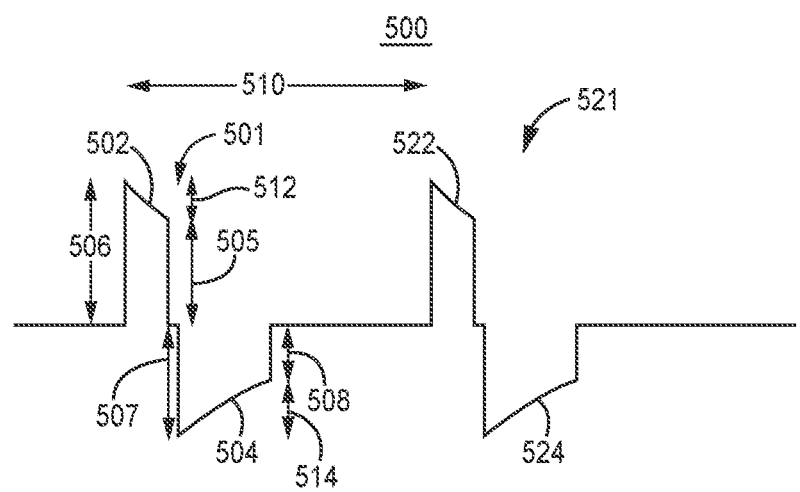
FIG. 10 is a diagram of a charge balanced pacing pulse delivery technique according to another example.

FIG. 10 is a diagram 500 of a charge balanced pacing pulse delivery technique that may be performed at block 106 of FIG. 7 by ICD 14 according to another example. A first pulse 502 and second pulse 504 of FIG. 10 are the first phase and second phase, respectfully of a balanced biphasic pacing pulse 501. The first pulse 502 has a leading voltage amplitude 506 and is terminated by HV therapy module 83 according to a programmed tilt 512 that is less than the tilt 514 of the second phase 504 of biphasic pacing pulse 501. For example, the first pulse 502 may be terminated according to a 25% tilt 512 when the trailing voltage amplitude 505 reaches 75% of the leading voltage amplitude 506.

The first pulse 502 is terminated, and the second pulse 504 is started by switching the polarity of the pacing load via control of switching circuitry 204 as described above in conjunction with FIG. 6. The leading voltage amplitude 507 of the second pulse 504 is approximately equal to the trailing voltage amplitude 505 of the first pulse 502.

The programmed tilt 514 of the second pulse 504 is different than the tilt 512 of the first pulse 502. Given the example above of a first phase tilt of 25%, the second pulse 504 may have a tilt of 53%, for example, such that the second pulse 504 is terminated when the trailing pulse amplitude 508 of the second pulse 504 reaches 47% of the second pulse leading voltage amplitude 507. Using two different tilts 512 and 514 of the first and second phases, respectively, of a biphasic pacing pulse results in a first pulse 502 that is charge balanced by a second, longer pulse 504 that is opposite in polarity from the first pulse 502. The next pacing pulse 521 is delivered at a pacing interval 510 and is similarly a charge balanced biphasic pacing pulse having a first pulse 522 and second pulse 524 that balances the charge delivered during the first pulse 522 of the biphasic pulse 521. Other examples of first and second tilts given above for controlling two monophasic pulses having opposite polarity may be used in controlling the two phases of a biphasic pulse such as pacing pulses 501 and 521. The first and second tilts may be predetermined such that no computations are made between the first phase pulse 502 and the second phase pulse 504 of a given biphasic pulse 501.

Figure 11:
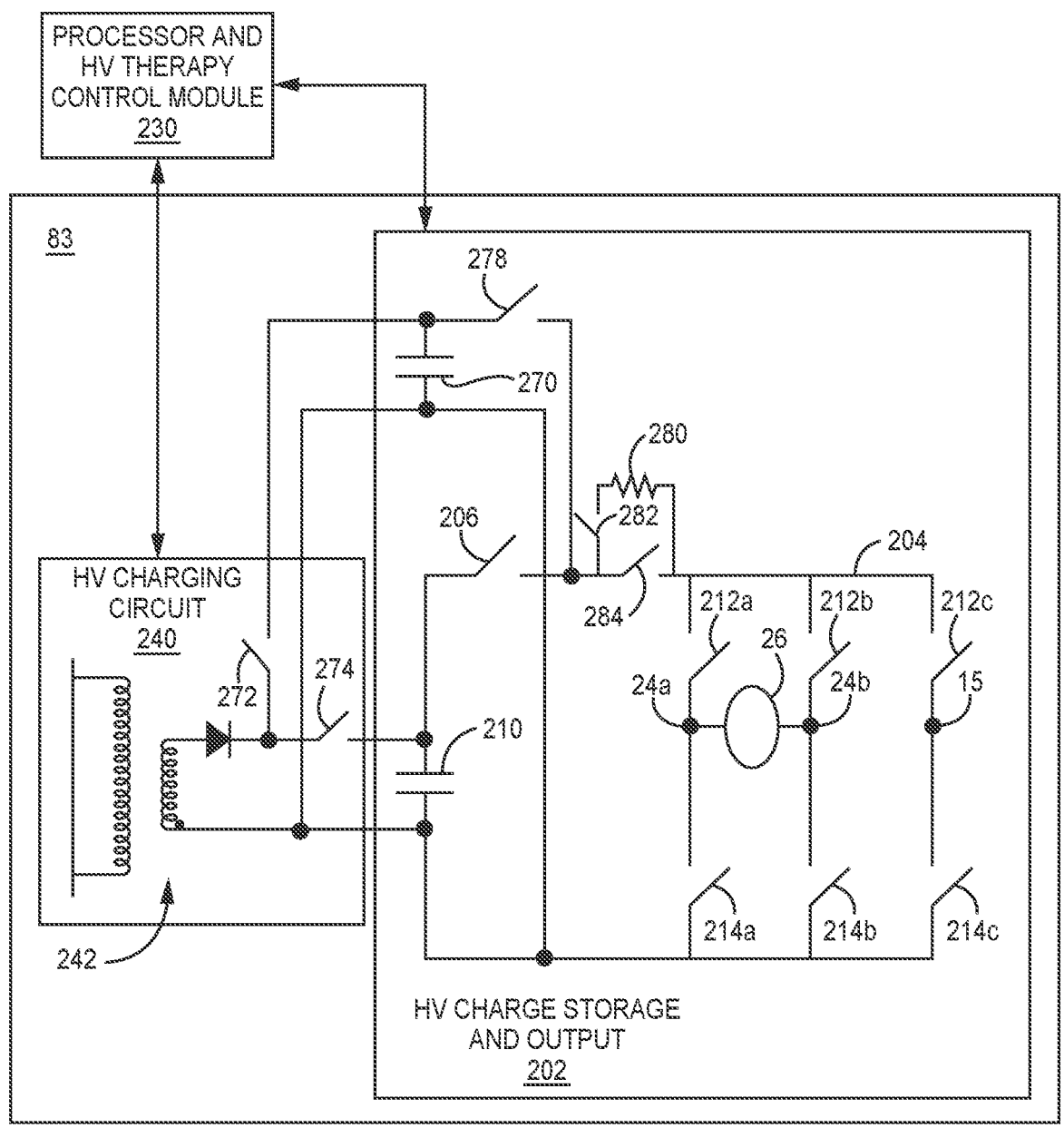
FIG. 11 is a diagram of another example of a HV therapy module that includes a charge balancing holding capacitor for delivering charge balancing pulses during a refractory period following a pacing pulse.

FIG. 11 is a diagram 201 of another example of a HV therapy module 83 that includes a charge balancing holding capacitor 270 for delivering charge balancing pulses during a refractory period following a pacing pulse. In the examples of the charge balanced pacing technique of FIG. 9A, the second pulse 404 is delivered after a short interpulse interval 414 so that it occurs during the myocardial refractory period. The leading voltage amplitude 406 is the same for the first pulse 402 and the second pulse 404, requiring recharging of the HV capacitor 210 in the HV therapy module 83 of FIG. 6.

In FIG. 11, a second capacitor 270 is included in HV therapy module 83 for generating a charge balancing pulse following a cardiac pacing pulse. The second capacitor 270 may be charged by HV charging circuit 240 to the same pacing voltage amplitude that HV capacitor 210 is charged to for delivering a first pulse, e.g., pulse 402 in FIG. 9A, that captures and paces the heart. The HV charging circuit 240 may include capacitor charging control switches 272 and 274 for controlling which capacitor 210 or 270 is being charged and preventing the charge of one capacitor from charging the other capacitor.

In some cases, HV charging circuit 240 may include a first charging circuit for charging HV capacitor 210 and a second charging circuit for charging second capacitor 270. The second charging circuit may include a step-up transformer, switches, rectifier, diodes and other components included in the architecture of the HV charging circuit 240. Alternatively, a second charging circuit included in HV charging circuit 240 for charging second capacitor 270 may include a state machine or capacitor charge pump circuit for charging the second capacitor 270 to a multiple of the battery voltage. The second capacitor 270 may have a higher capacitance than the holding capacitors included in the LV therapy module 85 and a higher breakdown voltage for allowing second capacitor 270 to be charged to a pacing voltage amplitude that is as high as the pacing voltage amplitude that the HV capacitor 210 is charged to.

Switch 274 may be enabled or closed to charge capacitor 210, which is subsequently discharged across a pacing electrode vector via switching circuitry 204 to deliver a monophasic or biphasic pacing pulse that captures the patient's heart. Pulse control switch 206 may control the width of the pacing pulse by controlling how long the capacitor 210 is coupled to switching circuitry 204.

Switch 274 is opened and switch 272 is closed to charge capacitor 270. Charging of both capacitors 210 and 270 may occur during a pacing interval, e.g., during pacing interval 410 of FIG. 9A. In this way, charging of second capacitor 270 does not need to occur during a short interpulse interval, such as interval 414 in FIG. 9A. After the first pulse, e.g., pulse 402, is delivered by discharging HV capacitor 210, the second pulse, e.g., pulse 404, is delivered by discharging second capacitor 270 across the pacing electrode vector via switching circuitry 204, which reverses the polarity of the pacing electrode vector for charge balancing. A second pulse control switch 278 controls when and for how long the second capacitor 270 is coupled to the switching circuitry 204 for delivering the second pulse 404.

While second capacitor 270 is shown as a single capacitor, it is recognized that one or more capacitors may be provided, e.g., in series or in parallel or combination thereof, to have a desired effective capacitance represented by second capacitor 270. The second capacitor 270 may have a capacitance that is smaller than HV capacitor 210 since capacitor 270 does not need to be charged to a shock voltage amplitude for delivering CV/DF pulses. Second capacitor 270 may have a capacitance greater than the holding capacitors used in LV therapy module 85 so that second capacitor 270 can be charged to the same pacing pulse voltage amplitude that HV capacitor 210 is charged to for delivering the first pulse 402 that captures and paces the heart. In some examples, the second capacitor 270 has a capacitance in the range of 148 to 155 microfarads, the same or similar to HV capacitor 210, but may have a lower voltage rating, and subsequently smaller size, than HV capacitors 210 since second capacitor 270 will not be charged to a shock voltage amplitude like HV capacitor 210.

In the example of FIG. 9A, the second pulse 404 has the same leading voltage amplitude 406 and pulse width 412 (but opposite polarity) as the first pulse 402 for balancing the charge delivered during the first pulse 402. In other examples, the second capacitor 270 may be charged to a lower voltage or a higher voltage than the leading voltage amplitude 406 of first pulse 402 and may have a pulse width that is longer or shorter, respectively, than the pulse width 412. A lower voltage amplitude of the second pulse 404 may conserve the power source 98 of ICD 14, but a longer pulse width of the second pule 404 may provide the required charge balancing. In other examples, a higher leading voltage amplitude of the second pulse 404 may be used to allow the second pulse 404 to be shorter in pulse width, e.g., to avoid extending the second pulse 404 beyond the physiological refractory period of the myocardium or into the vulnerable period associated with myocardial repolarization.

In other examples, processor and HV therapy control module 230 controls the charging of HV capacitor 210 to the programmed pacing voltage amplitude by initially charging HV capacitor 210 (by HV charging circuit 240) to a voltage greater than the programmed pacing voltage amplitude then electrically coupling HV capacitor 210 to second capacitor 270 via switches 272 and 274 to partially discharge HV capacitor 210 to charge second capacitor 270 from HV capacitor 210. Charge monitoring circuitry included in HV charging circuit 240 is used to monitor the charge of HV capacitor 210 and second capacitor 270. HV capacitor 210 may be charged to a first voltage greater than the pacing voltage amplitude, then discharged across second capacitor 210 down to the pacing voltage amplitude as second capacitor 210 is charged to the pacing voltage amplitude (or another leading voltage amplitude of the charge balancing second pulse).

After both capacitors 210 and 270 are each charged to their respective voltage amplitudes, HV capacitor 210 may be discharged to deliver the first pacing pulse of a pair of charge balanced pulses, e.g., pulse 402 of FIG. 9A. After a short interpulse interval, e.g., interval 414 of FIG. 9A, the second capacitor 270 is discharged to deliver the second pulse of the pair of charge balanced pulses, e.g., pulse 404 of FIG. 9A. The charge balancing second pulse may be delivered during the physiological refractory period such that it does not contribute to capture or pacing of the patient's heart, as shown in FIG. 9A. The second pulse delivered by second capacitor 270 may alternatively be a monophasic or biphasic pacing pulse delivered at a pacing interval after the first pulse to capture and pace the heart, such as second pulses 304 and 354, respectively, as shown in FIG. 8A or 8B.

The optional shunt resistance 250/252 shown in FIG. 6 is omitted from HV therapy module 83 in the example of FIG. 11. It is understood, however, that a shunt resistance as described in conjunction with FIG. 6 may be included in the HV therapy module 83 as shown in FIG. 11, which also includes second capacitor 270 for delivering the second, charge balancing pulse.

In the example of FIG. 11, a series resistance 280 that can be coupled in series with switching circuitry 204 via control of switches 282 and 284 is shown. Series resistance 280 may be switched in by switches 282 and 284 to increase the pacing load impedance during discharging of HV capacitor 210 and/or second capacitor 270. Increasing the pacing load impedance increases the RC time constant of the pacing circuit which has the effect of slowing the discharge rate of the HV capacitor 210 or second capacitor 270. The voltage amplitude of the second pulse delivered by HV capacitor 210 or by second capacitor 270 may be monitored during delivery of the second pulse. Alternatively or additionally, the pacing load impedance may be monitored during delivery of a first and/or second pulse of a pair of charge balanced pulses. If the decay rate of the voltage amplitude is faster than expected or the pacing impedance drops below a threshold, the series resistance 280 may be switched in by closing switch 282 and opening switch 284 to avoid depletion of the discharging capacitor 210 or 270 (or premature opening of enabled switches of switching circuitry 204) prior to completion of the first pacing pulse and/or completion of the charge balancing second pulse. It is contemplated that series resistance 280 may be switched in by controlling switches 282 and 284 (by processor and HV therapy control 230) before or during the first pacing pulse and/or before or during the charge balancing second pulse.

Figure 12:
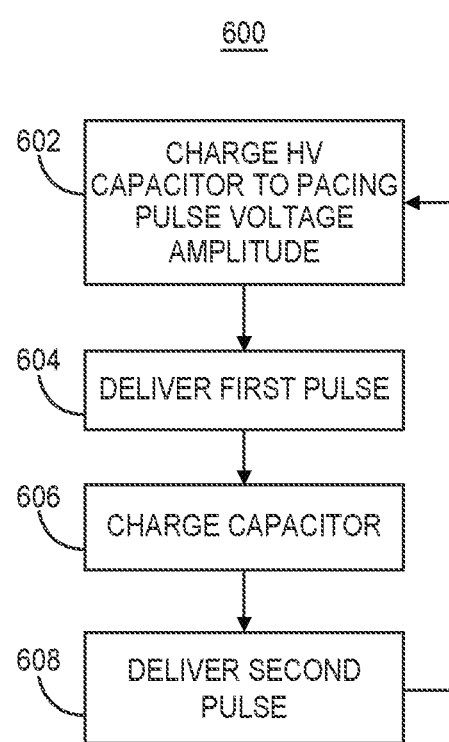
FIG. 12 is a flow chart of a method for delivering charge balanced cardiac pacing by a HV therapy module of an extra-cardiovascular ICD system.

FIG. 12 is a flow chart 600 of a method for delivering charge balanced cardiac pacing by a HV therapy module 83 of ICD 14. As described above, the charge balanced cardiac pacing includes a first pulse having a first polarity and a second pulse having a second polarity opposite the first polarity. The first pulse is delivered to capture and pace the heart. The second pulse is delivered to balance the charge delivered during the first pulse and may or may not contribute to pacing and capturing the heart. At block 602, the HV capacitor 210 of HV therapy module 83 is charged to a pacing pulse voltage amplitude. At the expiration of a cardiac pacing timing interval, the first pulse is delivered at block 604 by discharging the HV capacitor 210 for a predetermined pulse width or according to programmed tilt.

In some examples, capacitor charging is performed at block 606, which may be after delivery of the first pulse. The capacitor charged at block 606 may be the HV capacitor 210, which may be recharged to the pacing pulse voltage amplitude. The HV capacitor 210 may be recharged during a pacing interval, e.g., pacing interval 310 shown in FIGS. 8A and 8B, in preparation for delivering the second pulse as a second pacing pulse for capturing and pacing the heart after the pacing interval expires. In other examples, HV capacitor 210 may be recharged during an interpulse interval, e.g., interval 414 shown in FIG. 9A, in preparation for delivering the second pulse during the myocardial refractory period, for balancing the charge delivered during the first pulse but without contributing to capturing or pacing the heart.

In still other examples, the capacitor charged at block 606 may be a second capacitor 270 included in the HV therapy module 83 for generating and delivering charge balancing second pulses following first pulses delivered for pacing the heart. When a second capacitor 270 is used for delivering the charge balancing second pulses, the capacitor charging at block 606 may begin before delivery of the first pulse at block 604. For example, the HV capacitor 210 and the second capacitor 270 of FIG. 11 may be charged sequentially during a pacing interval, e.g., pacing interval 310 of FIG. 8A, pacing interval 360 of FIG. 8B or pacing interval 410 shown in FIG. 9A.

In other examples, charging of a capacitor at block 606 in preparation for delivering the second pulse may not be required. In the examples of FIG. 9B and FIG. 10, the charge balancing second pulse 434 and 504, respectively, is delivered using the remaining charge on the HV capacitor 210 for delivering the second pulse 434 or 504 having the opposite polarity of the first pulse 402 or 502, respectively.

The second pulse is delivered at block 608 by controlling the switching circuitry 204 to switch the polarity of the pacing electrode vector used to deliver the first pulse at block 604. The second pulse may be delivered by discharging HV capacitor 210 for a predetermined pulse width or according to a programmed tilt as described above. In other examples, the second pulse is delivered by discharging the second capacitor 270 shown in FIG. 11.

The processor and HV therapy control 230 may control HV charge storage and output module 202 to close a pulse control switch 206 to deliver the charge balancing second pulse at the expiration of a pacing interval, e.g., pacing interval 310 or 360 of FIGS. 8A and 8B. In other examples, pulse control switch 206 (or pulse control switch 278 when second capacitor 270 is used for delivering the second pulse) may be closed at the expiration of the interpulse interval 414 to start delivery of the second pulse 404 or 434 (FIG. 9A or 9B, respectively) as a charge balancing pulse during the myocardial refractory period. In the example of FIG. 10, the switching circuitry 204 is controlled to switch the polarity of the pacing electrode vector to start the second pulse 504 at block 608 as the HV capacitor 210 is being discharged. After delivering the charge balancing second pulse at block 608, the process returns to block 602 and may recharge the HV capacitor 210 (and in some cases second capacitor 270) to the pacing pulse voltage amplitude in preparation for the next scheduled pacing pulse.

Thus, a method and apparatus for controlling and delivering charge balanced cardiac pacing pulses by a high voltage therapy module of an extra-cardiovascular ICD system have been presented in the foregoing description with reference to specific embodiments. In other examples, various methods described herein may include steps performed in a different order or combination than the illustrative examples shown and described herein. The various components of the HV therapy module presented here may be combined in different combinations than the particular combinations described here. It is appreciated that various modifications to the referenced embodiments may be made without departing from the scope of the disclosure and the following claims.

The invention claimed is:

1. An extra-cardiovascular implantable cardioverter defibrillator (ICD) system comprising:
   a sensing module configured to receive a cardiac electrical signal from a patient's heart;
   a high voltage therapy module including:
      a first capacitor having a first capacitance and being chargeable to a shock voltage amplitude;
      a high voltage charging circuit configured to charge the first capacitor to the shock voltage amplitude for delivering a cardioversion/defibrillation shock pulse; and
      switching circuitry configured to couple the first capacitor to a pacing electrode vector selected from implantable extra-cardiovascular electrodes;
   a control module coupled to the sensing module and the high voltage therapy module and configured to:
   detect a need for cardiac pacing from the cardiac electrical signal;
   in response to detecting the need for cardiac pacing, control the high voltage therapy module to deliver at least one charge balanced cardiac pacing pulse via the pacing electrode vector by:
      controlling the high voltage charging circuit to charge the first capacitor to a pacing voltage amplitude that is less than the shock voltage amplitude;
      enabling the switching circuitry to discharge the first capacitor to deliver a first pulse having a first polarity and a first leading voltage amplitude corresponding to the pacing voltage amplitude for pacing the patient's heart; and
      controlling the high voltage therapy module to deliver a second pulse after the first pulse, the second pulse having a second polarity opposite the first polarity, the second pulse balancing an electrical charge delivered during the first pulse for pacing the patient's heart.

2. The system of claim 1, wherein the control module is configured to control the high voltage therapy module to deliver the second pulse by:
  recharging the first capacitor to the pacing voltage amplitude during a pacing interval following the first pulse;
  controlling the switching circuitry to reverse the polarity of the pacing electrode vector for delivering the second pulse; and
  delivering the second pulse upon expiration of the pacing interval after the first pulse, the second pulse having a second polarity opposite the first polarity and a second leading voltage amplitude corresponding to the pacing voltage amplitude to pace the patient's heart.

3. The system of claim 2, wherein the control module is configured to control the high voltage therapy module to:
  terminate the first pulse in response to the first leading voltage amplitude decaying by a predetermined percentage of the first leading voltage amplitude; and
  terminate the second pulse in response to the second leading voltage amplitude decaying by a predetermined percentage of the second leading voltage amplitude.

4. The system of claim 2, wherein the control module is configured to control the high voltage therapy module to deliver each of the first pulse and the second pulse as biphasic pulses by controlling the switching circuitry to switch the polarity of the pacing electrode vector during each one of the respective first pulse and second pulse.

5. The system of claim 1, wherein the control module is configured to control the high voltage therapy module to deliver the second pulse by:
  recharging the first capacitor after the first pulse; and
  enabling the switching circuitry to discharge the first capacitor during a physiological refractory period of the patient's heart following the first pulse.

6. The system of claim 5, wherein the control module is configured to control the high voltage therapy module to deliver each one of the first pulse and the second pulse as a monophasic pulse.

7. The system of claim 1, wherein the control module is configured to control the high voltage therapy module to deliver the second pulse by:
  terminating the first pulse in response to the first leading voltage amplitude decaying by a first predetermined percentage of the first leading voltage amplitude to a trailing voltage amplitude;
  switching the polarity of the extra-cardiovascular electrodes by the switching circuitry to start the second pulse having an opposite polarity of the first pulse and a second leading voltage amplitude corresponding to the trailing voltage amplitude; and
  terminating the second pulse in response to the second leading voltage amplitude decaying by a second predetermined percentage of the second leading voltage amplitude, the second predetermined percentage greater than the first predetermined percentage.

8. The system of claim 7, wherein the control module is configured to control the high voltage therapy module to deliver the first pulse and the second pulse as a first phase and a second phase, respectively, of a biphasic pacing pulse having a pulse energy greater than a capture threshold of the patient's heart.

9. The system of claim 1, wherein the control module is configured to control the high voltage therapy module to:
  deliver the first pulse according to a predetermined first pulse width;
  determine a second pulse width for controlling delivery of the second pulse to balance the electrical charge delivered during the first pulse; and
  deliver the second pulse having the second pulse width.

10. The system of claim 1, wherein the high voltage therapy module comprises a second capacitor coupled to the switching circuitry, wherein the control module is configured to control the high voltage therapy module to:
  charge the second capacitor; and
  deliver the second pulse by discharging the second capacitor.

11. The system of claim 10, wherein the control module controls the high voltage therapy module to charge the second capacitor to the pulse voltage amplitude and discharge the second capacitor to deliver the second pulse during a myocardial refractory period subsequent to the first pulse.

12. The system of claim 10, wherein the control module controls the high voltage therapy module to charge the first capacitor to the pacing voltage amplitude and charge the second capacitor by:
  charging the first capacitor to a voltage greater than the pacing voltage amplitude;
  coupling the first capacitor to the second capacitor; and
  charging the second capacitor from the first capacitor by discharging the first capacitor to the pacing voltage amplitude.

13. The system of claim 1, wherein:
  the high voltage therapy module further comprises a series resistance and a control switch between the switching circuitry and the first capacitor;
  the control module is configured to:
    monitor one of a voltage amplitude of the second pulse and/or a pacing load impedance; and
    control the control switch to couple the series resistance in series between the switching circuitry and the first capacitor in response to one of the voltage amplitude of the second pulse falling below a voltage threshold and/or the pacing load impedance falling below an impedance threshold.

14. The system of claim 1, wherein the control module is configured to:
  determine whether charge balanced pacing criteria are satisfied;
  control the high voltage therapy module to deliver the charge balanced cardiac pacing pulse in response to the charge balanced pacing criteria being satisfied; and
  control the high voltage therapy module to deliver at least one non-charge balanced cardiac pacing pulse in response to the charge balanced pacing criteria not being satisfied.

15. The system of claim 14, wherein the control module is configured to determine whether the charge balanced pacing criteria are satisfied by at least one of:
  comparing the pacing pulse amplitude to a threshold amplitude,
  comparing a pacing pulse width to a threshold width,
  comparing a pacing rate to a threshold rate, and/or
  comparing a pacing load impedance to a threshold impedance.

16. The system of claim 14, wherein the control module is configured to determine whether the charge balanced pacing criteria are satisfied by:

determining a count of previously delivered non-charge balanced pacing pulses delivered by the high voltage therapy module;
comparing the count to a count threshold; and
determining that the charge balanced pacing criteria are satisfied in response to the count being equal to or greater than the count threshold.

17. The system of claim 14, wherein the control module is configured to:
determine a pacing therapy to be delivered in response to detecting the need for pacing;
compare the determined pacing therapy to the charge balanced pacing criteria; and
deliver the at least one charge balanced cardiac pacing pulse in response to the determined pacing therapy meeting the charge balanced pacing criteria.

18. The system of claim 1, wherein the control module is further configured to:
detect a need for a cardioversion/defibrillation shock pulse from the cardiac electrical signal;
control the high voltage therapy module to charge the first capacitor to the shock voltage amplitude in response to detecting the need for the cardioversion/defibrillation shock pulse; and
discharge the first capacitor charged to the shock voltage amplitude via the extra-cardiovascular electrodes to deliver the cardioversion/defibrillation shock pulse.

19. The system of claim 1, wherein the pacing electrode vector comprises at least two of a first defibrillation coil electrode, a second defibrillation coil electrode, or an electrically conductive housing of the ICD, the first and second defibrillation coil electrodes carried by an extra-cardiovascular lead.

20. The system of claim 1, wherein the control module is configured to:
set a pacing interval according to one of a bradycardia pacing interval, an anti-tachycardia pacing interval, a post-shock pacing interval, a tachyarrhythmia induction pacing interval, or a rate-responsive pacing interval;
determine expiration of the pacing interval; and
control the high voltage therapy module to deliver the first pulse in response to expiration of the pacing interval to pace the heart at the pacing interval.

21. A method performed by an extra-cardiovascular implantable cardioverter defibrillator (ICD) comprising:
receiving a cardiac electrical signal by a sensing module of the ICD from a patient's heart;
detecting a need for cardiac pacing by a control module of the ICD from the cardiac electrical signal;
in response to detecting the need for cardiac pacing, controlling a high voltage therapy module of the ICD to deliver at least one charge balanced cardiac pacing pulse by:
controlling a high voltage charging circuit to charge a first capacitor to a pacing voltage amplitude, the first capacitor chargeable to a shock voltage amplitude that is greater than the pacing voltage amplitude;
enabling switching circuitry of the high voltage therapy module to discharge the first capacitor to deliver a first pulse having a first polarity and a first leading voltage amplitude corresponding to the pacing voltage amplitude for pacing the patient's heart via a pacing electrode vector selected from implantable extra-cardiovascular electrodes; and
controlling the high voltage therapy module to deliver a second pulse after the first pulse, the second pulse having a second polarity opposite the first polarity, the second pulse balancing an electrical charge delivered during the first pulse for pacing the patient's heart.

22. The method of claim 21, further comprising:
recharging the first capacitor to the pacing voltage amplitude during a pacing interval following the first pulse;
controlling the switching circuitry to reverse the polarity of the pacing electrode vector for delivering the second pulse; and
delivering the second pulse upon expiration of the pacing interval after the first pulse, the second pulse having a second polarity opposite the first polarity and a second leading voltage amplitude corresponding to the pacing voltage amplitude to pace the patient's heart.

23. The method of claim 22, further comprising:
terminating the first pulse in response to the first leading voltage amplitude decaying by a predetermined percentage of the first leading voltage amplitude; and
terminating the second pulse in response to the second leading voltage amplitude decaying by a predetermined percentage of the second leading voltage amplitude.

24. The method of claim 23, further comprising:
delivering each one of the first pulse and the second pulse as a biphasic pulse by controlling the switching circuitry to switch the polarity of the pacing electrode vector during each one of the respective first pulse and second pulse.

25. The method of claim 21, wherein delivering the second pulse comprises:
recharging the first capacitor after the first pulse; and
enabling the switching circuitry to discharge the first capacitor during a physiological refractory period of the patient's heart following the first pulse.

26. The method of claim 25, further comprising delivering each one of the first pulse and the second pulse as a monophasic pulse.

27. The method of claim 21, further comprising:
terminating the first pulse in response to the first leading voltage amplitude decaying by a first predetermined percentage of the first leading voltage amplitude to a trailing voltage amplitude;
switching the polarity of the extra-cardiovascular electrodes by the switching circuitry to start the second pulse having a second leading voltage amplitude corresponding to the trailing voltage amplitude; and
terminating the second pulse in response to the second leading voltage amplitude decaying by a second predetermined percentage of the second leading voltage amplitude, the second predetermined percentage greater than the first predetermined percentage.

28. The method of claim 21, further comprising delivering the first pulse and the second pulse as a first phase and a second phase, respectively, of a biphasic pacing pulse having a pulse energy greater than a capture threshold of the patient's heart.

29. The method of claim 21, further comprising:
delivering the first pulse according to a predetermined first pulse width;
determining a second pulse width for controlling delivery of the second pulse to balance the electrical charge delivered during the first pulse; and
delivering the second pulse having the second pulse width.

30. The method of claim 21, further comprising:
charging a second capacitor of the high voltage therapy module by the charging circuitry; and delivering the second pulse by discharging the second capacitor.

31. The method of claim 30, further comprising:
charging the second capacitor to the pulse voltage amplitude; and discharging the second capacitor to deliver the second pulse during myocardial refractory period subsequent to the first pulse.

32. The method of claim 30, wherein charging the first capacitor to the pacing voltage amplitude and charging the second capacitor comprises:
charging the first capacitor to a voltage greater than the pacing voltage amplitude;
coupling the first capacitor to the second capacitor; and
charging the second capacitor from the first capacitor by discharging the first capacitor to the pacing voltage amplitude.

33. The method of claim 21, further comprising:
controlling a control switch to couple a series resistance in series between the switching circuitry and the first capacitor in response to one of the voltage amplitude of the second pulse falling below a voltage threshold and/or the pacing load impedance falling below an impedance threshold.

34. The method of claim 21, further comprising:
determining whether charge balanced pacing criteria are satisfied;
controlling the high voltage therapy module to deliver the charge balanced cardiac pacing pulse in response to the charge balanced pacing criteria being satisfied; and
controlling the high voltage therapy module to deliver at least one non-charge balanced cardiac pacing pulse in response to the charge balanced pacing criteria not being satisfied.

35. The method of claim 34, wherein determining whether the charge balanced pacing criteria are satisfied comprises at least one of:
comparing the pacing pulse amplitude to a threshold amplitude,
comparing a pacing pulse width to a threshold width;
comparing a pacing rate to a threshold rate, and/or
comparing a pacing load impedance to a threshold impedance.

36. The method of claim 34, wherein determining whether the charge balanced pacing criteria are satisfied comprises:
determining a count of previously delivered non-charge balanced pacing pulses delivered by the high voltage therapy module via the pacing electrode vector;
comparing the count to a count threshold; and
determining that the charge balanced pacing criteria are satisfied in response to the count being equal to or greater than the count threshold.

37. The method of claim 34, further comprising:
determining a pacing therapy to be delivered in response to detecting the need for pacing;
comparing the determined pacing therapy to the charge balanced pacing criteria; and
delivering the at least one charge balanced cardiac pacing pulse in response to the determined pacing therapy meeting the charge balanced pacing criteria.

38. The method of claim 21, further comprising:
detecting a need for a cardioversion/defibrillation shock pulse from the cardiac electrical signal;
controlling the high voltage therapy module to charge the first capacitor to the shock voltage amplitude in response to detecting the need for the cardioversion/defibrillation shock pulse; and
discharging the first capacitor charged to the shock voltage amplitude via the extra-cardiovascular electrodes to deliver the cardioversion/defibrillation shock pulse.

39. The method of claim 21, wherein delivering the at least one charge balanced pacing pulse via the pacing electrode vector comprises controlling the switching circuitry to couple at least two of a first defibrillation coil electrode, a second defibrillation coil electrode, or an electrically conductive housing of the ICD to the first capacitor, the first and second defibrillation coil electrodes carried by an extra-cardiovascular lead.

40. The method of claim 21, further comprising:
setting a pacing interval according to one of a bradycardia pacing interval, an anti-tachycardia pacing interval, a post-shock pacing interval, a tachyarrhythmia induction pacing interval, or a rate-responsive pacing interval;
determining expiration of the pacing interval; and
controlling the high voltage therapy module to deliver the first pulse in response to expiration of the pacing interval to pace the heart at the pacing interval.

41. A non-transitory, computer-readable storage medium comprising a set of instructions which, when executed by a control module of an extra-cardiovascular implantable cardioverter defibrillator (ICD), cause the ICD to:
receive a cardiac electrical signal by a sensing module of the ICD from a patient's heart;
detect a need for cardiac pacing of the ICD from the cardiac electrical signal;
in response to detecting the need for cardiac pacing, control a high voltage therapy module of the ICD to deliver at least one charge balanced cardiac pacing pulse by:
controlling a high voltage charging circuit to charge a capacitor to a pacing voltage amplitude, the capacitor chargeable to a shock voltage amplitude that is greater than the pacing voltage amplitude;
enabling switching circuitry of the high voltage therapy module to discharge the first capacitor to deliver a first pulse having a first polarity and a leading voltage amplitude corresponding to the pacing voltage amplitude for pacing the patient's heart via a pacing electrode vector selected from implantable extra-cardiovascular electrodes; and
controlling the high voltage therapy module to deliver a second pulse after the first pulse, the second pulse having a second polarity opposite the first polarity, the second pulse balancing an electrical charge delivered during the first pulse for pacing the patient's heart.

42. An extra-cardiovascular implantable cardioverter defibrillator (ICD) system comprising:
a sensing module configured to receive a cardiac electrical signal from a patient's heart;
a high voltage therapy module including:
a first capacitor having a first capacitance and being chargeable to a shock voltage amplitude;
a high voltage charging circuit configured to charge the first capacitor to the shock voltage amplitude for delivering a cardioversion/defibrillation shock pulse; and
switching circuitry configured to couple the first capacitor to a pacing electrode vector selected from implantable extra-cardiovascular electrodes;
a control module coupled to the sensing module and the high voltage therapy module and configured to:

detect a need for cardiac pacing from the cardiac electrical signal;

determine that charge balanced pacing criteria are satisfied;

in response to detecting the need for cardiac pacing and determining that the charge balanced pacing criteria are satisfied, control the high voltage therapy module to deliver at least one charge balanced cardiac pacing pulse via the pacing electrode vector by:

controlling the high voltage charging circuit to charge the first capacitor to a pacing voltage amplitude that is less than the shock voltage amplitude;

enabling the switching circuitry to discharge the first capacitor to deliver a first pulse having a first polarity and a first leading voltage amplitude corresponding to the pacing voltage amplitude for pacing the patient's heart; and controlling the high voltage therapy module to deliver a second pulse after the first pulse, the second pulse having a second polarity opposite the first polarity, the second pulse balancing an electrical charge delivered during the first pulse.

\* \* \* \* \*